US008812091B1

(12) United States Patent
Brodnick

(10) Patent No.: US 8,812,091 B1
(45) Date of Patent: Aug. 19, 2014

(54) MULTI-CHANNEL CARDIAC MEASUREMENTS

(71) Applicant: APN Health, LLC, Pewaukee, WI (US)

(72) Inventor: Donald Brodnick, Cedarburg, WI (US)

(73) Assignee: APN Health, LLC, Pewaukee, WI (US)

( * ) Notice: Subject to any disclaimer, the term of this patent is extended or adjusted under 35 U.S.C. 154(b) by 0 days.

(21) Appl. No.: 13/922,953

(22) Filed: Jun. 20, 2013

Related U.S. Application Data

(63) Continuation-in-part of application No. 13/842,994, filed on Mar. 15, 2013.

(51) Int. Cl.
*A61B 5/04* (2006.01)

(52) U.S. Cl.
USPC .......................................................... 600/509

(58) Field of Classification Search
USPC .......................................................... 600/509
See application file for complete search history.

(56) References Cited

U.S. PATENT DOCUMENTS

| 4,240,442 | A | 12/1980 | Andresen et al. |
|---|---|---|---|
| 4,374,382 | A | 2/1983 | Markowitz |
| 4,583,553 | A | 4/1986 | Shah et al. |
| 5,117,824 | A | 6/1992 | Keimel et al. |
| 5,365,426 | A | 11/1994 | Siegel et al. |
| 5,560,368 | A | 10/1996 | Berger |
| 5,701,907 | A | 12/1997 | Klammer |
| 6,526,313 | B2 | 2/2003 | Sweeney et al. |
| 6,937,888 | B2 | 8/2005 | Kohler et al. |
| 7,364,550 | B1 | 4/2008 | Turcott |
| 7,561,912 | B2 | 7/2009 | Schatz et al. |
| 7,610,084 | B2 | 10/2009 | Sweeney et al. |
| 7,792,571 | B2 | 9/2010 | Sweeney et al. |
| 7,890,170 | B2 | 2/2011 | Ettori et al. |
| 8,041,417 | B2 | 10/2011 | Jonckheere et al. |
| 8,064,995 | B1 | 11/2011 | Dupelle et al. |
| 8,137,269 | B2 | 3/2012 | Sheikhzadeh-Nadjar et al. |

(Continued)

FOREIGN PATENT DOCUMENTS

| EP | 1745740 A1 | 1/2007 |
|---|---|---|
| EP | 2047794 A1 | 4/2009 |

(Continued)

OTHER PUBLICATIONS

Pan et al. A Real-Time QRS Detection Algorithm. IEEEE Transactions on Biochemical Engineering. vol. BME-32, No. 3, Mar. 1985. <http://mirel.xmu.edu.cn/mirel/public/Teaching/QRSdetection.pdf>.

(Continued)

*Primary Examiner* — Robert N Wieland
(74) *Attorney, Agent, or Firm* — Jansson Munger McKinley & Shape Ltd.

(57) ABSTRACT

An automatic method of determining local activation time (LAT) in multi-channel cardiac electrogram signals including a plurality of cardiac channels, the method comprising: (a) storing the cardiac channel signals; (b) selecting a mapping channel, a ventricular channel, and a reference channel from among the plurality of cardiac channels; (c) using the selected channels to compute first LAT values at a plurality of mapping-channel locations; (d) monitoring the quality of at least one selected channel; (e) if the quality of a monitored cardiac channel falls below a standard, replacing the sub-standard channel with another channel of the plurality of channels having an above-standard quality; and (f) computing second LAT values based on the replacement cardiac channel.

50 Claims, 23 Drawing Sheets

(56) References Cited

U.S. PATENT DOCUMENTS

| | | |
|---|---|---|
| 8,150,503 B2 | 4/2012 | Schatz et al. |
| 2002/0138013 A1 | 9/2002 | Guerrero et al. |
| 2003/0216654 A1 | 11/2003 | Xu et al. |
| 2004/0015090 A1 | 1/2004 | Sweeney et al. |
| 2004/0059203 A1 | 3/2004 | Guerrero et al. |
| 2004/0186388 A1 | 9/2004 | Gerasimov |
| 2007/0161916 A1 | 7/2007 | Zantos et al. |
| 2008/0109041 A1 | 5/2008 | de Voir |
| 2010/0305645 A1 | 12/2010 | Sweeney et al. |
| 2011/0071375 A1 | 3/2011 | Baker, Jr. et al. |
| 2011/0137153 A1* | 6/2011 | Govari et al. ............ 600/424 |
| 2011/0172729 A1 | 7/2011 | Sweeney et al. |
| 2012/0123279 A1 | 5/2012 | Brueser et al. |
| 2012/0130263 A1 | 5/2012 | Pretorius et al. |
| 2012/0179055 A1 | 7/2012 | Tamil et al. |
| 2012/0197151 A1 | 8/2012 | Schatz et al. |
| 2013/0245477 A1 | 9/2013 | Brodnick et al. |

FOREIGN PATENT DOCUMENTS

| | | |
|---|---|---|
| WO | 199619939 A1 | 7/1996 |
| WO | 2005002669 A2 | 1/2005 |
| WO | 2011088043 A1 | 7/2011 |
| WO | 2012056342 A2 | 5/2012 |

OTHER PUBLICATIONS

Friesen G.M. et al. "A Comparison of the Noise Sensitivity of None QRS Detection Alogrithyms," IEEE Transactions on Biomedical Engineering, IEEE Inc. New York, US, Bd. 37, Nr. 1, 1990, Seiten 85-98.

* cited by examiner

| | | CL = 342 msec | | | | |
|---|---|---|---|---|---|---|
| ACT | $t_{M\text{-}ACT}$ | $t_{NV}$ | $D_P$ | $D_F$ | $A_{SC}$ | Comment |
| 132a | | | | | | not detected - too early |
| 132b | 4382 | 11 | 40 | 8 | -37 | beginning-of-data rule |
| 132c | 4732 | 314 | 8 | 16 | 290 | selected activation |
| 132d | 5058 | 12 | 16 | 11 | -15 | |
| 132e | 5411 | 320 | 11 | 247 | 62 | end-of-data rule |
| 132f | | | | | | not detected - too small |

[all values in the table in msec]

TABLE LEGEND

CL = reference-channel cycle length $t_{M\text{-}ACT}(i)$ = mapping-channel activation times $t_{V\text{-}ACT}(i)$ = ventricular-channel activation times $t_{NV}(i) = \min_{\text{all } t_{V\text{-}ACT}} (|t_{M\text{-}ACT}(i) - t_{V\text{-}ACT}|)$ = time to nearest ventricular-channel activation $D_P(i) = t_{M\text{-}ACT}(i) - t_{M\text{-}ACT}(i-1) - CL$ = deviation of prior interval from CL $D_F(i) = t_{M\text{-}ACT}(i+1) - t_{M\text{-}ACT}(i) - CL$ = deviation of future interval from CL $A_{SC}(i) = t_{NV}(i) - D_P(i) - D_F(i)$ = mapping-channel activation selection score

FIG. 8B

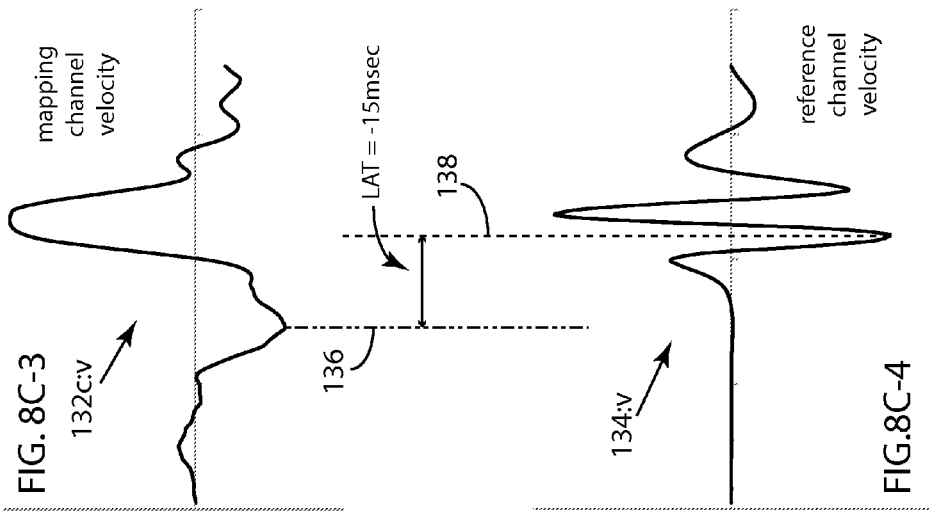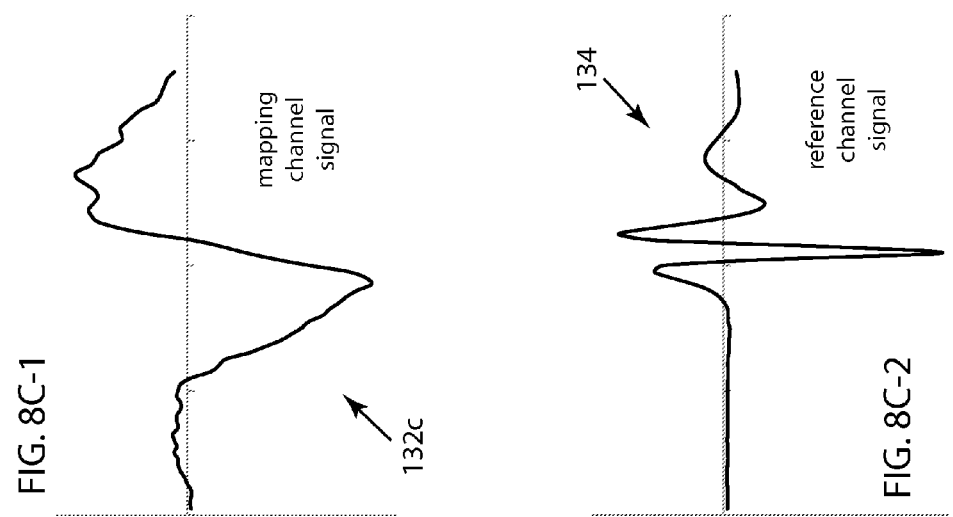

| | | | | | | | | | | | |
|---|---|---|---|---|---|---|---|---|---|---|---|
| A: | 451 | 1594 | 1994 | 2333 | 2678 | 3024 | 3368 | 3703 | 4050 | 4387 | 4731 | 5069 | 5412 | 5749 |
| B: | 4555 | 4672 | 4730 | 4727 | 4730 | 4734 | 4736 | 4729 | 4734 | 4729 | 4731 | 4727 | 4728 | 4723 |
| C: | 161 | 44 | -14 | -11 | -14 | -18 | -20 | -13 | -18 | -13 | -15 | -11 | -12 | -7 |
| | | | | | | | | ⎫ 214 | | | | | |
| D: | -20 | -18 | -18 | -15 | -14 | -14 | -13 | -13 | -12 | -11 | -11 | -7 | 44 | 161 |
| E: | | | | -15 | -14 | -14 | -13 | -13 | -12 | -11 | -11 | | | |

[All times in msec;   CL = 342 msec;   $t_M$ = 4716 msec]

TABLE LEGEND

Row A: fiducial times $t_R$ in reference channel of maximum negative velocity
Row B: adjusted fiducial times $t_{RA}$ (adjusted to within ±CL/2 of $t_M$ (CL = 342 msec; $t_M$ = 4716 msec)
Row C: intermediate LAT values = $t_M - t_{RA}$
Row D: ordered list of intermediate LAT values
Row E: interquartile set of intermediate LAT values measurement confidence interval = ±2 msec (range is -15 to -11)

FIG. 8D

Automatic Ventricular-Channel Selection

Automatic Ventricular-Channel Selection

Automatic Reference-Channel Selection

260

|  | $M_1$ | $M_2$ | $M_3$ | $M_4$ | $M_5$ | $M_6$ | $M_7$ | $M_8$ |
|---|---|---|---|---|---|---|---|---|
| $R_1$ | – | ✓ | ✓ | ✓ | ✓ | ✓ | ✓ | ✓ |
| $R_2$ | – | – | ✓ | ✓ | ✓ | ✓ | ✓ | ✓ |
| $R_3$ | – | – | – | ✓ | ✓ | ✓ | ✓ | ✓ |
| $R_4$ | – | – | – | – | ✓ | ✓ | ✓ | ✓ |
| $R_5$ | – | – | – | – | – | ✓ | ✓ | ✓ |
| $R_6$ | – | – | – | – | – | – | ✓ | ✓ |
| $R_7$ | – | – | – | – | – | – | – | ✓ |
| $R_8$ | – | – | – | – | – | – | – | – |

FIG. 12

MULTI-CHANNEL CARDIAC MEASUREMENTS

RELATED APPLICATION

This application is a continuation-in-part of application Ser. No. 13/842,994 filed on Mar. 15, 2013.

FIELD OF THE INVENTION

This invention is related generally to the field of electrophysiology, and more particularly to technology for accurate measurement of parameters within body-surface ECG, intracardiac, and epicardial electrical signals such as heart rates and local activation times and the assessment of the quality of such measurements.

BACKGROUND OF THE INVENTION

The invention disclosed herein involves the processing of multiple channels of electrical signals which are produced by the heart. These channel signals include the ECG signals from body-surface electrodes and signals from electrodes within the body, i.e., intracardiac signals from within vessels and chambers of the heart and epicardial signals from the outer surface of the heart. Throughout this document, the term "multi-channel cardiac electrogram" (or "MCCE") is used to refer to all of these types of channels, and when specific types are appropriate, specific nomenclature is used. This new terminology (MCCE) is used herein since the term "ECG" sometimes only refers to body-surface measurements of cardiac performance.

A major component in cardiac interventional procedures such as cardiac ablation is the display of cardiac data which is extracted from the MCCE signals captured by an array of electrodes placed on the body surface and within and on the structures of the heart itself. Among the important data which are displayed are ventricular pulse interval (time between heart beats), intracardiac cycle length (time between the activations in arrhythmias (such as atrial fibrillation), relative time differences between related activations in two intracardiac channels to generate activation maps, and assessments of signal strength, variability, and other measures of signal quality within MCCE signals.

Cardiac interventional electrophysiology procedures (e.g., ablation) can be extremely time-consuming, and the reliable determination and presentation of such cardiac parameters is an important element in both the quality of the procedures and the speed with which they can be carried out. Often the data which are presented to the electrophysiology doctor during such procedures exhibit high variability contributed not only by the performance of the heart itself but by unreliable detection of certain features of the MCCE signals. Therefore there is a need for more reliable and more rapid algorithms to process body surface and intracardiac signals obtained during an electrophysiology (EP) procedure.

MCCE electrodes capture the electrical signals in the cardiac muscle cells. As mentioned above, some MCCE electrodes may be attached to the body surface (ECG) and some may be positioned inside cardiac veins, arteries and chambers (intracardiac) and on the outer surface of the heart (epicardial) as conductive elements at the tips or along the lengths of catheters introduced into the body and maneuvered into position by the EP doctor. The electrical signals within the heart muscles and which flow therefrom to other regions of the body have very low voltage amplitudes and therefore are susceptible to both external signal noise and internally-generated electrical variations (non-cardiac activity). In addition, cardiac arrhythmias themselves may be highly variable, which can make reliable extraction of cardiac parameters from MCCE signals difficult.

One important cardiac parameter used during such procedures is the time difference between the activations occurring within two channels, both of which contain the electrical signals of an arrhythmia. This measurement is called local activation time (LAT), and measurement of a plurality of LATs is the basis for the generation of an activation map. The map displays information about the sequence of activations of cardiac muscle cells relative to each other, and this sequence of information is combined with physical anatomical position information to form the map. An activation map then provides guidance to the EP doctor for the process of applying therapies to heart muscle cells which can terminate cardiac arrhythmias and permanently affect the heart to prevent recurrence of such arrhythmias.

This entire process is referred to as mapping because all of the information generated by analysis of the MCCE signals is combined in a single computer display of a three-dimensional figure that has the shape of the heart chamber of interest and display of additional image qualities such as color that convey the sequence of electrical activity (activation map) or possibly other qualities of the electrical activity (e.g., voltage map). These images are similar in style to weather maps common today in weather-forecasting. Such a cardiac map becomes a focus of attention for the EP doctor as he directs the motion of catheters in the heart to new positions, and an algorithm which processes the MCCE signals produces measurements from the electrodes in new positions. As this process continues, the map is updated with new colored points to represent additional information about the electrical activity of the heart.

The generation of position information and its combination with the cardiac timing information is outside the scope of the present invention. The focus of the present invention is the processing of MCCE signals to measure time relationships within the signals, the two most important of which are cycle length (CL) and local activation time (LAT).

Currently-available MCCE-processing algorithms are simplistic and often provide inaccurate measurements which cause the activation map and many other cardiac parameter values to be misleading. A misleading map may either (1) compel the doctor to continue mapping new points until apparent inconsistencies of the map are corrected by a preponderance of new, more-accurately measured map points or (2) convince the doctor to apply a therapy to a muscle region which actually makes little or no progress in the termination of an arrhythmia, again prolonging the procedure while the EP doctor maps more points in an attempt to locate new regions where therapy may be effective.

Currently, computer systems which assist doctors in the mapping process have manual overrides to allow a technician, or sometimes the EP doctor himself, to correct the measurements made by the system automatically. This requires a person to observe a computer display called the "Annotation Window" which shows a short length of the patient's heart rhythm, perhaps 3-5 heart beats as recorded in 3-8 channels (signals from MCCE electrodes).

The channels of the annotation window are of several types. Usually there will be a body surface ECG lead such as lead II that identifies when ventricular activity is occurring. (It is also possible that the ventricular activity may be sensed by an intracardiac channel electrode.) There is one channel, identified as a reference channel, the electrode of which remains in a fixed position during the entire mapping-generating procedure. There is at least one other intracardiac channel (the mapping channel) which senses the electrical signal at a catheter tip, the precise three-dimensional position of which is determined by other means. The electrical activity in the mapping channel is compared to the activity in the reference channel to determine the local activation time (LAT) which is used to color the map at that precise three-dimensional position.

Intracardiac channels may be of either the bipolar or unipolar recording types, and the inventive measurement method disclosed herein can be applied to both types of signals. Also, since it is possible during arrhythmias for some chambers of the heart to be beating in a rhythm different from other chambers of the heart, the annotation window often contains additional channels to aid the doctor's interpretation of the data presented.

OBJECTS OF THE INVENTION

It is an object of this invention, in the field of electrophysiology, to provide an automatic method for accurate measurement of several parameters which characterize MCCE signals.

Another object of this invention is to provide an automatic method for such measurements which operates rapidly enough to not hinder an electrophysiologist performing procedures which utilize such a method.

Another object of this invention is to provide an automatic method for rapid and reliable measurement of cardiac cycle length (or heart rate).

Another object of this invention is to provide an automatic method for rapid and reliable measurement of cardiac parameters to reduce the length of time certain cardiac procedures require and also reduce the X-ray exposure times for the patients.

Another object of this invention is to provide an automatic method for rapid and reliable measurement of local activation times which are provided for the rapid generation of local activation time maps, determining the precise phase relationship between a reference channel and a mapping channel.

Still another object of this invention is to provide an automatic method for cardiac parameter measurement which can be used in real time during certain interventional cardiac procedures.

Another object of this invention is to provide an automatic method for rapid and reliable activation mapping which can continue providing LAT measurement when a reference signal degrades such that it is no longer useable as a reference signal.

Another object of this invention is to provide an automatic method for rapid and reliable activation mapping which can continue providing LAT measurement when a ventricular signal degrades such that it is no longer a useable signal.

Yet another object of the invention is to provide an automatic method for measuring cardiac parameters which is largely insensitive to the amplitude of the MCCE signals and almost entirely dependent on the timing information contained in such signals.

These and other objects of the invention will be apparent from the following descriptions and from the drawings.

SUMMARY OF THE INVENTION

The term "digitized signal" as used herein refers to a stream of digital numeric values at discrete points in time. For example, an analog voltage signal of an MCCE channel is digitized every millisecond (msec) using an analog-to-digital (A/D) converter to generate a series of sequential digital numeric values one millisecond apart. The examples presented herein use this sampling rate of 1 kHz, producing streams of digital values one millisecond apart. This sampling rate is not intended to be limiting; other sampling rates may be used.

The term "velocity" as used herein refers to a signal the values of which are generally proportional to the time-rate-of-change of another signal.

The term "velocity-dependent signal" as used herein refers to a set of possible signals which relate to the velocity of a channel signal, and in particular, retain certain properties of channel velocity. Channel signals are filtered to generate velocity-dependent signals which contain signal information which does not lose either the positive or negative activity in a channel signal. One such velocity-dependent signal is the absolute value of channel velocity; such a velocity-dependent signal is used in some embodiments of the inventive method to preserve the magnitude of the activity in a signal. Other possible velocity-dependent signals are even powers of velocity (squared, $4^{th}$ power, etc.) which retain both the positive and negative signal activity in a velocity signal—the relative magnitudes are not critical in the present invention as long as both positive and negative activity within the signals are not masked by the filtering. Numerous other possible filtering strategies may be used to generate velocity-dependent signals, such as comparison of positive portions of the velocity with respect to a positive threshold and similarly, comparison of negative portions of the velocity with respect to a negative threshold. With respect to their use in the present invention, all velocity-dependent signals as defined herein are fully equivalent to absolute-value velocity filtering in every relevant respect.

The term "two differenced sequential boxcar filters" as used herein refers to two boxcar filters which operate in tandem and then the difference between the two boxcar filter values is computed. Such a filtering operation is one embodiment by which a low-pass filter followed by a first-difference filter is applied. Two differenced sequential boxcar filters are illustrated in FIG. 3A and described in detail later in this document.

The term "dot-product autocorrelation" as used herein refers to a mathematical operation applied to a time series of digital values, and this operation is generally a signal-processing application of conventional autocorrelation. Applying conventional autocorrelation to a fixed-length time series of numeric values $x_i$ generates another series of numeric values $a_j$ which represents how well the signal $x_i$ correlates with itself as a function of the time difference between the signal and the same signal displaced in time by a period of time called lag. In conventional autocorrelation of a fixed-length signal $x_i$ having n values in a time interval, $$a_j \Sigma(x_i \cdot x_{i-j})$$

where the symbol $\Sigma$ indicates the sum over all n-j values of $x_i$, i represents values of time, and j represents values of lag. As used herein, the dot-product autocorrelation may be adjusted by a scale factor K as a computational convenience, in which case, $$a_j = K \cdot \Sigma(x_i \cdot x_{i-j})$$

again where the symbol $\Sigma$ indicates the sum over all n-j values of $x_i$, i represents values of time, and j represents values of lag. Such an adjustment is not intended to be limiting to the meaning of the term. The maximum value of $a_j$ is, of course, $a_0$ since at lag=0, the signal perfectly correlates with itself.

One such form of scale factor may include $a_0$ such that $K=k/a_0$ where k is a constant and its value is set for computational convenience.

The term "magnitude-coincidence autocorrelation" as used herein refers to a modification of dot-product autocorrelation. As used herein, magnitude-coincidence autocorrelation operates on signals which first have been rectified (an absolute-value filter has been applied). Each numeric value of a fixed-length time series $x_i$ (all values of $x_i \geq 0$) is replaced by a 1 if the value $x_i$ is equal to or greater than a threshold value $T_{AC}$ and by a 0 if $x_i$ is less than $T_{AC}$. Further, threshold $T_{AC}$ is set at some multiple of the median of all n values of $x_i$ in the fixed-length time series. Rectified cardiac signals such as those processed by the present invention contain noise which is typically substantially smaller than the peaks within such signals. Furthermore, over all n values of such a signal, a large number of values will be close to the noise level since there are substantial periods of time between signal (electrical events) representing a heart beat. Therefore, if threshold $T_{AC} = p \cdot \text{median}(x_i)$ and p is, e.g., 4, threshold $T_{AC}$ will be just above the baseline noise in the signal $x_i$, and the thresholded signal $X_i$ will be equal to 1 only if a non-zero signal value is present which is generally not noise. Then, the magnitude-coincidence autocorrelation will have peaks for values of lag at which the time-distribution of the noise-free signal aligns (correlates well) with itself. Magnitude-coincidence autocorrelation is particularly useful when the "time" information in a signal is of more interest than the "shape" or amplitude information in a signal.

The term "normal median" as used herein refers to the numeric value determined from a set of numeric values, such numeric value (median) being computed according to the commonly-understood mathematical meaning of the term median. The normal median of a finite set of numeric values can be determined by arranging all the numeric values from lowest value to highest value and picking the middle value from the ordered set. If there is an even number of numeric values in the set, the normal median is defined to be the mean of the two middle values of the ordered set.

The term "set-member median" as used herein refers to the numeric value determined from a set of numeric values in a manner modified from the above-described method of median determination. In this modified determination, if there is an even number of numeric values in the set, the set-member median is either one of the two middle values in the ordered set such that the set-member median is always a member of the set of numeric values.

The term "intracardiac channel" as used herein refers to a channel of a set of MCCE signals which is connected to an internal lead, i.e., connected to a internal-surface electrode such as is at the end or along the tip of a cardiac catheter. For example, such an electrode may be in a blood vessel or in a chamber of a heart.

The term "ventricular channel" as used herein refers to a channel of a set of MCCE signals which exhibits the dominant response of the ventricles. This may most often be a channel which is connected to an external lead, i.e., connected to a body-surface electrode. An epicardial or intracardiac channel may also sometimes be a ventricular channel.

The term "activation" as used herein refers to a time segment within an MCCE signal which represents the passage of a depolarization wavefront within muscle cells adjacent to an MCCE electrode. An activation may sometimes be referred as an activity trigger.

The term "cycle length" as used herein refers to the time between neighboring activations in an MCCE signal, particularly in a reference-channel or mapping-channel signal. As used herein, the term "pulse interval" is used to connote the cycle length for a ventricular channel. The terms "ventricular pulse interval" and "intracardiac cycle length" are used to distinguish between these two measures of repetitive signals. For example, if a cardiac patient is in a period of atrial fibrillation or flutter, there may be a significant difference between the rate of occurrence of electrical events in a ventricular channel and in some intracardiac channels. The ventricular cycle length, herein called ventricular pulse interval to further distinguish it from intracardiac cycle length, may be two or three times as long as the intracardiac cycle length.

As used herein, the terms "method" and "process" are sometimes used interchangeably, particularly in the description of the preferred embodiment as illustrated in the figures. The algorithms described as embodiments of the inventive automatic method of measuring parameters of multi-channel cardiac electrogram signals are presented as a series of method steps which together comprise processes.

As used herein, the terms "signal" and "channel" may be used interchangeably since the inventive automatic method described herein uses signal values in the channels of MCCE signals.

The present invention is an automatic method of determining local activation time (LAT) in multi-channel cardiac electrogram signals which include a plurality of cardiac channels. The method comprises: (a) storing the cardiac channel signals; (b) selecting a mapping channel, a ventricular channel, and a reference channel from among the plurality of cardiac channels; (c) using the selected channels to compute first LAT values at a plurality of mapping-channel locations; (d) monitoring the quality of at least one selected channel; (e) if the quality of a monitored cardiac channel falls below a standard, replacing the sub-standard channel with another channel of the plurality of channels having an above-standard quality; and (f) computing second LAT values based on the replacement cardiac channel. In certain embodiments, computing second LAT values based on the replacement cardiac channel includes computing second LAT values for previous mapping-channel locations. Certain other embodiments include displaying the first LAT values as a first LAT map, and if second LAT values are computed, generating a second LAT map based on the second LAT values. In certain embodiments, the replaced and replacement channels are reference channels.

In some preferred embodiments of the inventive method, monitoring the signal quality of a cardiac channel includes: (a) generating a velocity-dependent signal from the monitored channel signal over a preset time window; (b) finding the median value MED of the velocity-dependent signal over the preset time window; (c) dividing the velocity-dependent signal into a plurality of signal chunks; (d) finding the chunk-maximum within each chunk; (e) finding the maximum MAX and minimum MIN values among the plurality of chunk-maxima; and (f) computing a channel signal quality SQ based on MAX, MIN and MED. In some of these embodiments, the channel signal quality SQ is computed as $2 \times \text{MIN} - \text{MAX} - K_1 \times \text{MED}$ where $K_1$ is a constant. In some of these embodiments, each signal chunk is of equal length; in some embodiments, there may be three chunks of equal length.

In certain preferred embodiments of the inventive method, computing second LAT values based on the replacement cardiac channel includes computing second LAT values for previous mapping-channel locations.

Some preferred embodiments of the inventive method also include displaying the first LAT values as a first LAT map, and if second LAT values are computed, generating a second LAT map based on the second LAT values.

In some highly-preferred embodiments of the inventive method, the preset time window is about 6 seconds long, in such embodiments, the channel signal quality is computed as $2 \times MIN - MAX - K_1 \times MED$ where $K_1$ is a constant. $K_1$ may have a value of about 4.

In certain highly-preferred embodiments of the inventive automatic LAT-determination method, monitoring the quality of cardiac channels includes monitoring cycle-length variability of each channel of a first subset of the monitored channels. In some embodiments, the first-subset cycle-length variability monitoring includes determining a maximum cycle length $MAX_{CL}$, a minimum cycle length $MIN_{CL}$, and a cycle-length variability $VAR_{RC}$ for each monitored first-subset channel. In some of these embodiments, determining a maximum cycle length $MAX_{CL}$, a minimum cycle length $MIN_{CL}$, and a cycle-length variability $VAR_{RC}$ includes for each monitored first-subset channel: (a) selecting a set of sequential sub-signals; (b) estimating cycle lengths and cycle-length variability for each sub-signal; (c) selecting $MAX_{CL}$ and $MIN_{CL}$ as the maximum and minimum of the sub-signal cycle lengths; and (d) selecting $VAR_{RC}$ as the maximum sub-signal variability.

In some preferred embodiments, estimating the cycle length of each sub-signal includes: (a) estimating pulse intervals in the ventricular channel; (b) generating a velocity-dependent signal from the sub-signal over a preset time window; (c) autocorrelating the sub-signal velocity-dependent signal; (d) selecting a peak value of the autocorrelation based on ventricular pulse-interval estimates; and (e) setting the sub-signal cycle length CL to the lag value of the selected peak in the autocorrelation. Further, in some of these embodiments, estimating sub-signal cycle-length variability includes: (i) estimating the lag DCL at an autocorrelation peak near twice CL; (ii) computing an intermediate cycle-length $CL_A$; and (iii) computing sub-signal cycle-length variability as the absolute value of the difference between CL and $CL_A$.

The sub-signals may be of equal length, may be about 6 seconds long, and there may five such sub-signals in the first-subset cycle-length variability determination process.

In some preferred embodiments, monitoring the quality of cardiac channels further includes for each first-subset channel: (a) determining a signal quality value $SQ_i$ for each sub-signal; (b) summing the sub-signal signal quality values $SQ_i$ to generate a first-subset channel signal quality value $SQ_{RC}$; and (c) computing a first-subset channel figure-of-merit $FM_{RC}$. The figure-of-merit $FM_{RC}$ may be computed as $SQ_{RC}/K_2 - MAX_{CL} - MIN_{CL} - K_3 \times VAR_{RC}$ where $K_2$ and $K_3$ are constants; the value of $K_2$ may be about 32; the value of $K_3$ may be about 2. In some of these embodiments, if the quality of a monitored first-subset channel falls below a standard, the sub-standard first-subset channel is replaced with another first-subset channel having a higher figure-of-merit.

In some highly-preferred embodiments of the inventive method, monitoring the quality of cardiac channels includes monitoring pulse-interval variability of each channel of a second subset of the monitored channels. In some of these embodiments, the second-subset pulse-interval variability monitoring includes for each monitored second-subset channel: (a) selecting a set of sequential sub-signals; (b) for each sub-signal, determining a maximum pulse interval $MAX_{Ei}$ and a minimum pulse-interval $MIN_{Ei}$; (b) for each sub-signal, computing a sub-signal pulse-interval variability $VAR_i$ as $MAX_{Ei} - MIN_{Ei}$; and (c) computing a second-subset channel pulse-interval variability $VAR_{VC}$ as the maximum value among the sub-signal pulse-interval variability values $VAR_i$. Further, in some of these embodiments, monitoring the quality of cardiac channels further includes for each second-subset channel (i) determining a signal quality value $SQ_i$ for each sub-signal and (ii) summing the sub-signal signal quality values $SQ_i$ to generate a second-subset channel signal quality value $SQ_{VC}$. Then, in some embodiments, if the quality of a monitored second-subset channel falls below a standard, the sub-standard second-subset channel is replaced with another second-subset channel having a higher channel signal quality $SQ_{VC}$. In some such embodiments, the channel pulse-interval variability $VAR_{VC}$ of the another second-subset channel is below a computed threshold pulse-interval variability $T_{VC}$. In some embodiments, threshold $T_{VC}$ is proportional to the median of all second-subset channel pulse-interval variability values $VAR_{VC}$.

In some preferred method embodiments, monitoring the quality of cardiac channels further includes monitoring pulse-interval variability of each channel of a second subset of the monitored channels.

In some highly-preferred embodiments of the inventive automatic LAT determination method, monitoring the quality of a cardiac channel includes estimating an LAT measurement confidence interval and comparing the estimate with a measurement-confidence criterion. In some of these embodiments, estimating an LAT measurement confidence interval includes: (a) estimating the cycle-length CL of the reference channel; (b) selecting an activation at a time $t_M$ in the mapping-channel signal; (c) identifying a plurality of activations at times $t_R$ in the reference channel; (d) computing a plurality of LAT values with respect to the values of $t_R$; (d) selecting a subset of the plurality of LAT values; and (e) estimating the LAT measurement confidence interval as the difference between the maximum and minimum LAT values in the subset. In some embodiments, the subset comprises the inter-quartile values of the plurality of LAT values.

In other highly-preferred embodiments, monitoring the quality of a cardiac channel includes estimating a channel cycle-length confidence interval. In some of these embodiments, estimating a channel cycle-length confidence interval includes estimating channel cycle-length by: (a) estimating pulse intervals in the ventricular channel; (b) generating a velocity-dependent signal from the channel signal over a preset time window; (c) autocorrelating the channel velocity-dependent signal; (d) selecting a peak value of the autocorrelation based on ventricular pulse-interval estimates; and (e) setting the channel cycle length CL to the lag value of the selected peak in the autocorrelation. Further, in some of these embodiments, estimating a channel cycle-length confidence interval includes (i) determining the lag value L2 at a peak in the autocorrelation near twice CL and (ii) estimating the channel cycle-length confidence interval as $\pm(L2-2CL)$.

In some other highly-preferred embodiments, monitoring the quality of a cardiac channel includes estimating a channel pulse-interval confidence interval. In some of these embodiments, estimating a channel pulse-interval confidence interval includes estimating channel pulse-interval by: (a) generating a velocity-dependent signal from the channel signal over a preset time window; (b) identifying a plurality of activation times in the channel velocity-dependent signal; (c) computing a set of activation intervals; (d) identifying maximum and minimum activation intervals in the set; and (e) setting the confidence interval equal to the difference between the maximum and minimum activation intervals.

In another aspect of this invention, the invention is an automatic method of measuring parameters of multi-channel cardiac electrogram signals which include at least one ventricular channel and at least two other cardiac channels. The inventive method comprises: (a) digitizing a first other cardiac signal and a ventricular-channel signal over a first preset time window; (b) filtering the ventricular-channel signal to generate a ventricular absolute-value velocity signal and filtering the digitized first other cardiac signal to generate a first other cardiac absolute-value velocity signal; (c) estimating a pulse interval in the ventricular absolute-value velocity signal; (d) autocorrelating the first other cardiac absolute-value velocity signal; (e) selecting a peak value of the autocorrelation based on ventricular pulse-interval estimates; and (f) setting the cycle length of the first other cardiac signal to the lag value of the selected peak in the autocorrelation.

In some embodiments of the inventive method, the absolute-value velocity signals are each generated by applying a low-pass filter followed by a first-difference filter and an absolute-value filter. In some of these embodiments, each combination of low-pass filter and first-difference filter is two differenced sequential boxcar filters.

In highly-preferred embodiments of the inventive method, the first signal autocorrelation is calculated by magnitude-coincidence autocorrelation. In some other embodiments, the first signal autocorrelation is calculated by dot-product autocorrelation.

In certain preferred embodiments, the step of estimating the pulse interval includes determining ventricular-channel activations by measuring signal threshold-crossings. In some of these preferred embodiments, determining the ventricular-channel activations includes the steps of subdividing the first preset time window into three equal-length periods of time, determining the signal maximum in each of the three periods of time, setting the threshold to a fixed threshold-percentage of the minimum of the three signal maxima, and identifying ventricular-channel activation times at threshold-crossing times at which a threshold-crossing is preceded by at least a fixed below-threshold period. In some of these embodiments, the fixed threshold-percentage is about 50%, and in some, the below-threshold period is about 120 msec.

In other preferred embodiments, estimating the pulse interval includes the steps of computing all activation double-intervals, determining the median of all of the activation double-intervals, and setting the pulse interval to one-half of the median.

Some preferred embodiments of the inventive method include a step of determining a confidence interval for the pulse interval estimate. This determination comprises computing a set of activation intervals, identifying maximum and minimum activation intervals in the set, and setting the confidence interval equal to the difference between the maximum and minimum activation intervals.

In highly-preferred embodiments, selecting a peak value of the autocorrelation includes the steps of: (1) determining the lag W of the minimum of the autocorrelation for lag less than a preset lag threshold; (2) determining the maximum peak $P_1$ of the autocorrelation for lag $CL_1$ greater than W and setting an interim cycle length CL to $CL_1$ and an interim peak $P_{CL}$ to $P_1$; (3) determining whether $CL_1$ is within a first lag interval of twice the pulse interval; (4) finding maximum $P_2$ in the autocorrelation at lag $CL_2$ within a second lag interval of the pulse interval, determining (a) whether the maximum $P_2$ is greater than $P_{CL}/2$ and (b) whether $CL_2$ is within a third lag interval of $CL_1/2$, and if (a) and (b) are true, setting CL to $CL_2$ and $P_{CL}$ to $P_2$; (5) determining whether CL is within a fourth lag interval of the pulse interval; (6) finding maximum $P_3$ in the autocorrelation at lag $CL_3$ between a lag of CL/6 and a lag of 2CL/3, determining (a) whether the maximum $P_3$ is greater than $P_{CL}/2$ and (b) whether either $2CL_3$ or $3CL_3$ is within a fifth lag interval of CL, and if both (a) and (b) are true, setting CL to $CL_3$; and (7) setting the cycle length of the first other cardiac signal to interim cycle length CL.

In certain highly-preferred embodiments of the inventive method, the first other cardiac signal is a reference signal and a second other cardiac signal is a mapping signal. In these embodiments, the method further includes the steps of: (a) computing a reference velocity signal; (b) selecting the mapping signal over a second preset time window, the second preset time window being a percentage of and overlapping the end of the first preset time window; (c) digitizing the mapping signal; (d) filtering the digitized mapping signal to generate a mapping velocity signal and an absolute-value mapping velocity signal; (e) determining mapping-signal activations by measuring signal threshold-crossings; (f) selecting a mapping-signal activation based on its time relative to the ventricular channel activation times; (g) finding time $t_M$ of the maximum negative velocity in the selected mapping-signal activation; (h) finding the time $t_R$ of the maximum negative velocity in the reference velocity signal within one half of the cycle length of the reference signal; and (i) computing local activation time as $t_M$ minus $t_R$. Some of these embodiments include storing and displaying the local activation time in a map and repeating steps (a) through (i) to store and display plural local activation times in a map.

Some embodiments of the inventive method include finding a plurality of times $t_R$, computing a plurality of interim local activation times $T_{LAT}$ based on the times $t_R$, and determining the local activation time based on a subset of the plurality of times $t_{LAT}$. In some of these embodiments, the single local activation time is the median of the plurality of interim times $t_{LAT}$ and in some, the plurality of times $t_R$ includes all of the times of local negative velocity maxima in the reference signal, and the subset includes times $T_{LAT}$ based on each time $t_R$. Further, in some, the plurality of times $t_R$ includes all of the times of local negative velocity maxima in the reference signal, and the subset includes times $T_{LAT}$ based on an interquartile set of times $T_{LAT}$.

In another aspect of the inventive method, wherein the at least one ventricular channel includes two or more ventricular channels, the method further includes automatically selecting the ventricular-channel signal from among the two or more ventricular channels. In some embodiments, the step of selecting the ventricular-channel signal comprises: (1) digitizing a plurality of candidate ventricular-channel signals over a first preset selection time window; (2) filtering each of the plurality of candidate signals to generate corresponding candidate absolute-value velocity signals; (3) dividing each candidate absolute-value velocity signal into a set of sequential, equal-length sub-signals; (4) estimating signal quality and pulse interval for each sub-signal of each candidate signal; (5) combining the sub-signal quality estimates of each candidate signal to generate a signal quality estimate $SQ_{VC}$ for each candidate signal; (6) determining the maximum and minimum pulse intervals for each sub-signal and generating a pulse interval variability estimate $VAR_{VC}$ for each candidate signal by selecting the maximum difference between sub-signal pulse-interval maxima and minima; (7) excluding candidate ventricular-channel signals with values $VAR_{VC}$ above a variability threshold; and (8) selecting the ventricular channel as the non-excluded candidate channel with the highest signal quality estimate $SQ_{VC}$. In some of these embodiments, estimating signal quality for each sub-signal comprises the steps of dividing each sub-signal into three equal-length chunks, determining the maximum of each chunk, determining the maximum MAX and minimum MIN of the three chunk maxima, computing the median of the sub-signal to generate a noise estimate $N_S$ equal to twice the median, and calculating the signal-quality estimate as $2 \times MIN - MAX - 2 \times N_S$.

Certain preferred embodiments of the inventive method include automatically selecting the first other cardiac channel from among the at least two other cardiac channels. In certain of these embodiments, selecting the first other cardiac channel comprises: (1) digitizing a plurality of candidate other cardiac signals over a first preset selection time window; (2) filtering each of the plurality of candidate signals to generate corresponding candidate absolute-value velocity signals; (3) dividing each candidate velocity signal into a set of sequential, equal-length sub-signals; (4) estimating signal quality, cycle length and cycle-length variability for each sub-signal of each candidate signal; (5) combining the sub-signal quality estimates of each candidate signal to generate a signal quality estimate $SQ_{RC}$ for each candidate signal; (6) determining the maximum $MAX_{CL}$ and minimum $MIN_{CL}$ of the sub-signal cycle lengths and a cycle-length variability $VAR_{RC}$ for each candidate signal; (7) calculating a figure of merit value for each candidate signal based on signal quality $SQ_{RC}$, $MAX_{CL}$, $MIN_{CL}$, and $VAR_{RC}$; and (8) selecting the other cardiac channel as the candidate channel with the highest figure of merit value.

In another aspect of the inventive method, wherein the at least two other cardiac channels includes three or more other cardiac channels, the method further includes selecting a reference channel and a mapping channel from among the other cardiac channels, monitoring the signal quality of each of the reference channel and at least one of the other cardiac channel, and if the signal quality of the reference channel falls below a signal quality threshold, replacing the reference channel with the other cardiac channel with a higher signal quality and calculating local activation time values based on the higher-signal-quality other cardiac channel.

In a further aspect of the inventive method, wherein multi-channel cardiac electrogram signals include a plurality of cardiac channels and at least one ventricular channel, a reference channel is automatically selected from the plurality of cardiac channels based on signal quality, cycle length, and cycle-length variability measurements of a subset of the plurality of cardiac channels. In some such embodiments, the at least one ventricular channel is two or more ventricular channels the method further includes automatically selecting a ventricular channel based on signal quality and variability of the ventricular channels.

In yet another aspect of the inventive method of automatic measurement of parameters of multi-channel cardiac electrogram signals, wherein there is a plurality of cardiac channels, some preferred embodiments include measuring and storing cardiac parameters in a first subset of channels, detecting activations in a second subset of channels, and computing local activation times for a plurality of pairs of channels, each pair including one channel from the first subset of channels and one channel from the second subset of channels.

BRIEF DESCRIPTION OF THE DRAWINGS

FIG. 8B is a table which illustrates the process by which a specific mapping-channel activation is selected for the determination of LAT for the example of FIG. 8A.

FIG. 8C-1 through FIG. 8C-4 is a set of plots illustrating in detail a selected mapping-channel activation and its corresponding portion of the reference-channel signal which, as illustrated in FIGS. 8A and 8B, are used to determine LAT for a single mapping point.

FIG. 8D is a table illustrating an embodiment of a method to assess measurement confidence in the inventive method of FIG. 1, using the examples of FIG. 8A through FIG. 8C-4. FIG. 8D also illustrates a second alternative embodiment of the inventive method to determine an LAT value for a single mapping point.

FIG. 12 is a matrix which schematically illustrates a series of reference channels and mapping channels among a set of MCCE signals which in an aspect of the inventive method may be processed in parallel to generate multiple LAT maps by various combinations of reference and mapping channels.

DETAILED DESCRIPTION OF PREFERRED EMBODIMENTS

Figure 1:
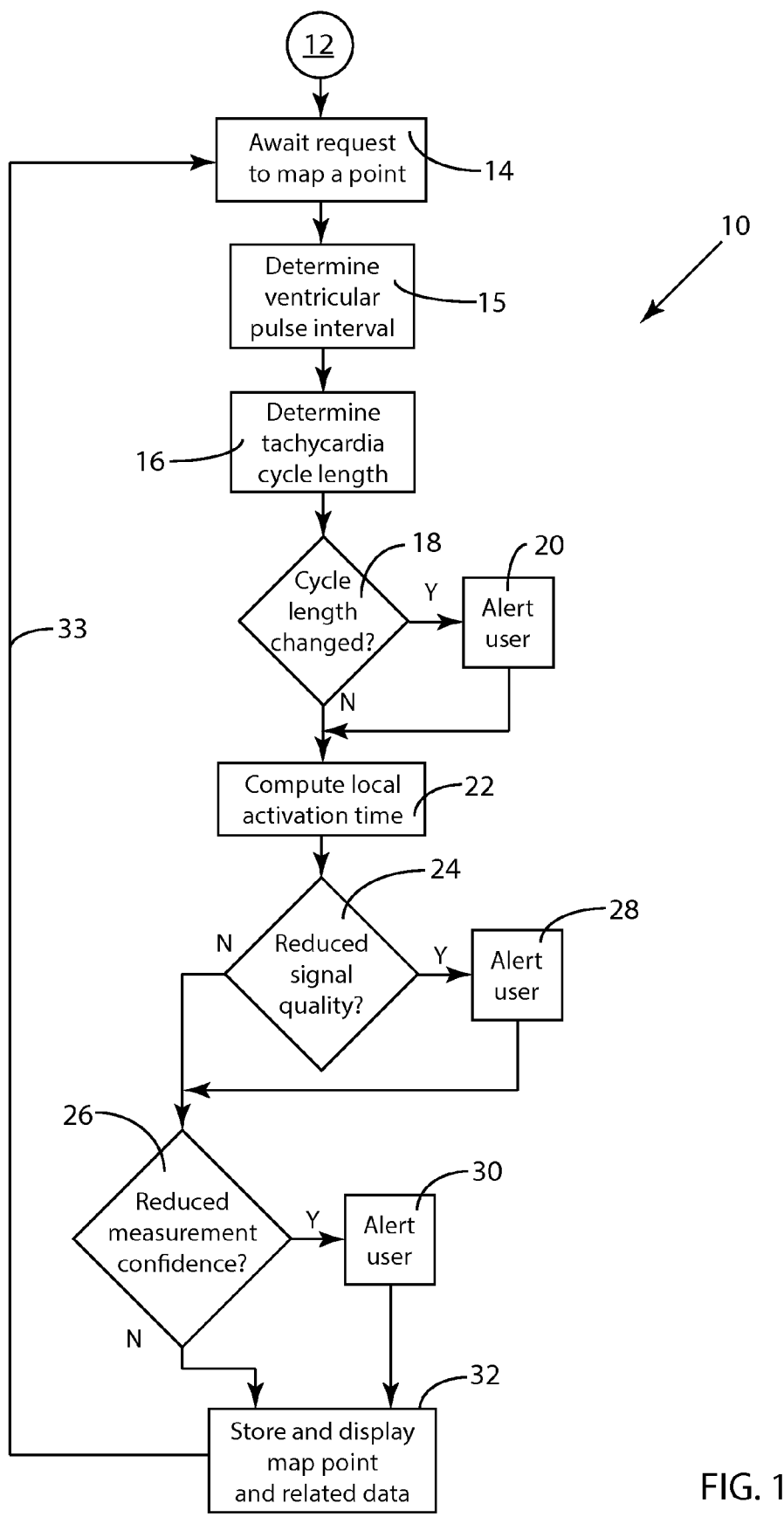
FIG. 1 is a schematic block diagram of the inventive method for measuring parameters of MCCE signals, including intracardiac cycle lengths and local activation times and estimates of signal and measurement quality. The steps of the method as illustrated in the block diagram of FIG. 1 are further detailed in several other schematic block diagrams.

FIG. 1 illustrates one embodiment of the inventive method for measuring parameters of multi-channel ECG signals. FIG. 1 is a high-level schematic block diagram of a method which measures intracardiac cycle lengths and local activation times on a near-real-time basis as part of a system to generate maps (e.g., computer displayed 3D presentations of the distribution of voltages and activation times across cardiac structures) and provides feedback regarding signal quality and measurement confidence.

Several other figures in this document relate to the inventive method of FIG. 1, and the steps presented in the schematic block diagrams of these other figures are nested within the high-level schematic block diagram of FIG. 1, as will be described below. In addition, the inventive method also includes initial channel selection steps which occur prior to the steps of FIG. 1. These are illustrated and described later in this document, in FIGS. 9 through 11C.

Referring to FIG. 1, an embodiment 10 of the inventive method includes a flow loop of method steps which is initiated by a request 12 to map a point, and each time a mapping-point request 12 is generated, the method proceeds through the steps shown in FIG. 1. The flow chart element labeled with reference number 14 indicates that the flow loop waits to receive request 12. During a procedure in which the inventive method is used, an electrophysiologist (EP doctor) is maneuvering an electrode-tipped catheter (mapping catheter) through and around the chambers, arteries and veins of a patient's heart. The electrode on this maneuvered catheter provides the mapping-channel signal. When the EP doctor determines that the maneuvered catheter electrode is in a desired position, the EP doctor activates a signal as request 12 to map a point. A plurality of map points constitute the map.

Generating the map during this procedure involves time measurements made between the MCCE signals of the mapping electrode and a reference electrode. (As used herein, electrodes are positioned to provide signals to channels. Thus, for example, the mapping electrode provides the signal for the mapping channel.) The reference electrode is positioned before mapping begins in a location that is expected to remain constant during the mapping process and that will generate stable and repetitive electrical signals.

Each electrode develops an electrical signal when muscle cells in contact with the electrode change their cell membrane potentials. These electric potentials change as the cells mechanically contract. Nerve cells, which do not contract, also can be in contact with electrodes and produce electrical signals.

The map being generated represents a particular heart rhythm being studied, such as tachycardia. The reference-channel and mapping-channel signals are both cyclical and have substantially the same cycle length (CL). The reference-channel signal represents a zero-phase or index moment of the particular cardiac cycle, and the local activation time (LAT) measurements (time difference between mapping and reference-channel signals) indicate the sequence of muscle and nerve cell activation of various points (map points) in the cardiac structure. This time sequence and its physical course around the anatomy of the heart are the information the EP doctor needs to determine how to apply therapy. The term "local" refers to the fact that the measurement applies to the heart cells in contact with the electrode and to signals with respect to a reference-channel signal, and this information is translated to a position on a three-dimensional (3D) image of the heart chamber.

Activation time is measured relative to one or more activations at the reference electrode and may be positive or negative. A local activation time which is negative by more than a half of one cycle length may also be recognized as being positive at a corresponding time less than a half of one cycle length. Local activation times may be defined as being relative to the nearest activation in the reference channel.

Positioning of the mapping catheter is guided at times by fluoroscopic imaging. At a position of interest, the EP doctor generates request 12 to trigger the system to make measurements from the MCCE signals available from the maneuvered catheter and other more stationary catheters and body surface electrodes. These measurements at mapping points are represented graphically, usually by color, on a 3D image of the heart chamber of interest. These points may be requested at irregular intervals of several seconds to perhaps minutes, depending on when the EP doctor maneuvers the mapping catheter to a point at which measurements should be taken.

When request 12 is received, measurements are made using an "epoch" of the most recent 6 seconds of MCCE signals. In embodiment 10, the 6-second length of this epoch should not be taken as limiting. The epoch is a preset time window of MCCE signals, and its 6-second length is chosen here in embodiment 10 such that selected signals during the preset time window contain a suitable number of electrical events to permit the analysis to be performed. During such mapping procedure, at least one mapping channel and at least one reference channel are used. At some points within embodiment 10, as will be described later in this document, the epoch is divided into three equal periods of time, and six seconds is chosen here since a 2-second period will almost always contain at least one heart beat (or cell activation) for all heart rates above 30 beats per minute.

As the mapping catheter is moved, it is important that its electrode be in place at the selected location for a period of time (dwell time) long enough to obtain a suitable signal. In embodiment 10, such dwell time is about 2 seconds. Thus, when request 12 is received, the epoch consists of 6 seconds of data on other channels being used and 2 seconds of data on the mapping channel. (The 6 seconds of data may consist of the immediate past 4 seconds of the data plus 2 seconds of data generated after request 12 occurs. The 6 seconds of data in an epoch may also be the 6 seconds of data immediately preceding the request 12, since it may be that the mapping catheter has already been in a stable position for the 2 seconds prior to the triggering of request 12. Other possible strategies for acquiring the epochs of data are also possible.)

In the high-level schematic block diagram of FIG. 1, after request 12 is received, ending the wait in method step 14, a determination of the pulse interval in the ventricular channel is performed in method step 15. Details of ventricular pulse interval determination 15 are detailed in the schematic block diagrams and example signals of FIG. 2 through FIG. 5, all of which will be described later in this document.

Following ventricular pulse interval determination 15, a determination 16 of the intracardiac cycle length in the reference channel is performed. (Method step 16 is shown in FIG. 1 as determining tachycardia cycle length since the inventive method is intended primarily for monitoring cardiac parameters in the treatment of patients in tachycardia. The use of the term "tachycardia" is not intended to be limiting. The inventive method is applicable to measurement of all types of cardiac arrhythmias as well as normal heart rhythms.) Details of intracardiac cycle length determination 16 are detailed in the schematic block diagrams and example signals of FIGS. 2 through 4B and FIG. 6, all of which will be described later in this document. Intracardiac cycle length determination 16 depends on the value of ventricular pulse interval established in determination 15.

Decision step 18 follows determination 16 such that the cycle length determined in step 16 is compared to a cycle-length-change criterion in decision step 18, and if the cycle length has not exceeded the cycle-length-change criterion, the inventive method proceeds. If, however, the cycle-length-change criterion is exceeded, the EP doctor is alerted in method step 20 in order that steps may be taken by the EP doctor during the mapping procedure to evaluate the impact of such a change.

A cycle-length-change criterion applied in method step 18 may be based on an absolute time difference in cycle length from a previous cycle length or on the average of a plurality of previous cycle lengths. Or it may be based on a percentage change from such quantities. One useful previous cycle length is the initial or starting cycle length of the reference channel, established at the beginning of the mapping procedure. A local activation time map is related to a particular rhythm so that if there is too great a change in cycle length, the EP doctor may choose to start a new map, or in fact may determine that mapping is no longer appropriate at such time. A value for the percentage change which triggers an alert in method step 20 may be that the current reference-channel cycle length (determined in method step 16) is found to differ from the starting cycle length by more than 10%. Such value is not intended to be limiting; other values may be found to provide adequate warning to the EP doctor.

Embodiment 10 of the inventive method then proceeds to a computation 22 of the local activation time (LAT) associated with the map point being analyzed. Details of local activation time computation 22 are detailed in the schematic block diagram of FIGS. 7A-7C which will be described later in this document, and examples of such determination are illustrated in FIGS. 8A through 8D.

Embodiment 10 of the inventive method for measuring parameters of MCCE signals includes steps for evaluation 24 of signal quality and evaluation 26 of measurement confidence, both of which are applied within embodiment 10 to monitor the measurement process. In each case, that is, reduced signal quality as determined in step 24 and reduced measurement confidence in step 26, the EP doctor is alerted (user alerts 28 and 30, respectively) that such conditions have been detected. One embodiment of a method to measure signal quality in method step 24 is included in the steps illustrated in FIG. 4A and will be discussed later in this document. One embodiment of a method to assess measurement confidence in method step 26 is illustrated in the example of FIG. 8D described later in this document.

As shown in FIG. 1, the method of embodiment 10 provides (in step 32) the map point and its related measurement data to a computer at least for display to the EP doctor during the procedure and for storage in memory for later analysis. The system then returns via loop path 33 to wait for the next mapping point request 12 at step 14.

Figure 2:
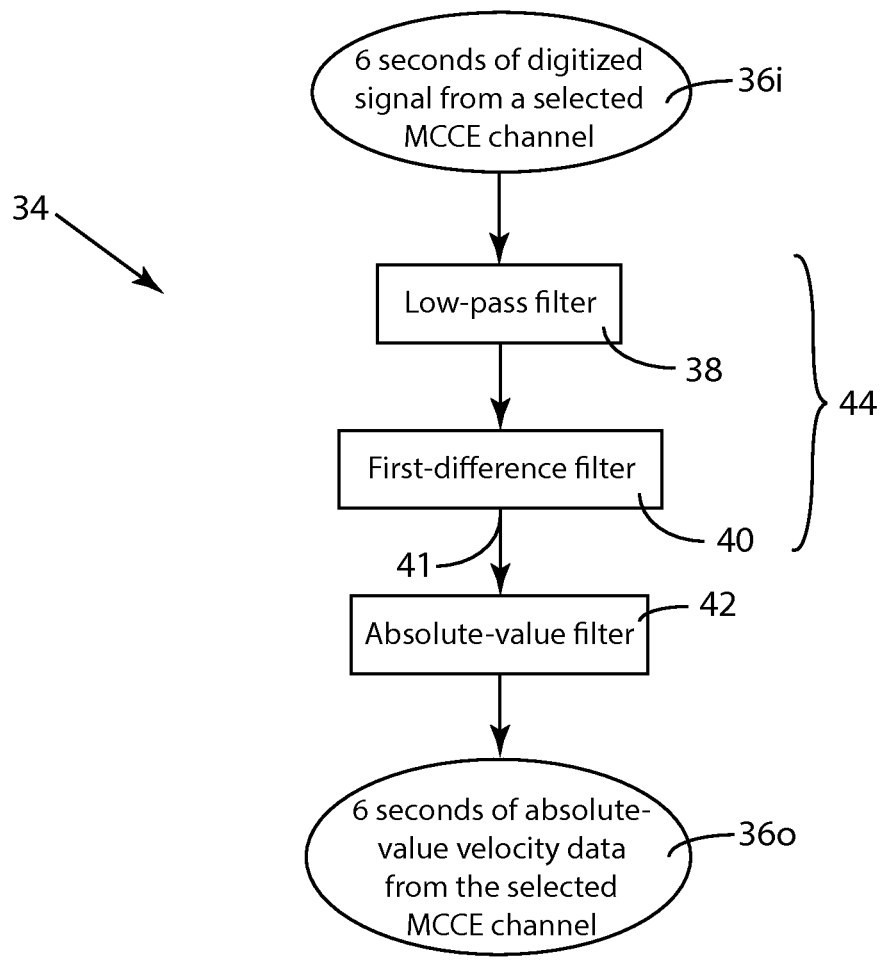
FIG. 2 is a schematic block diagram illustrating steps of the inventive method to generate absolute-value velocity data of a selected digitized MCCE signal.
Figures 3A, 3B:
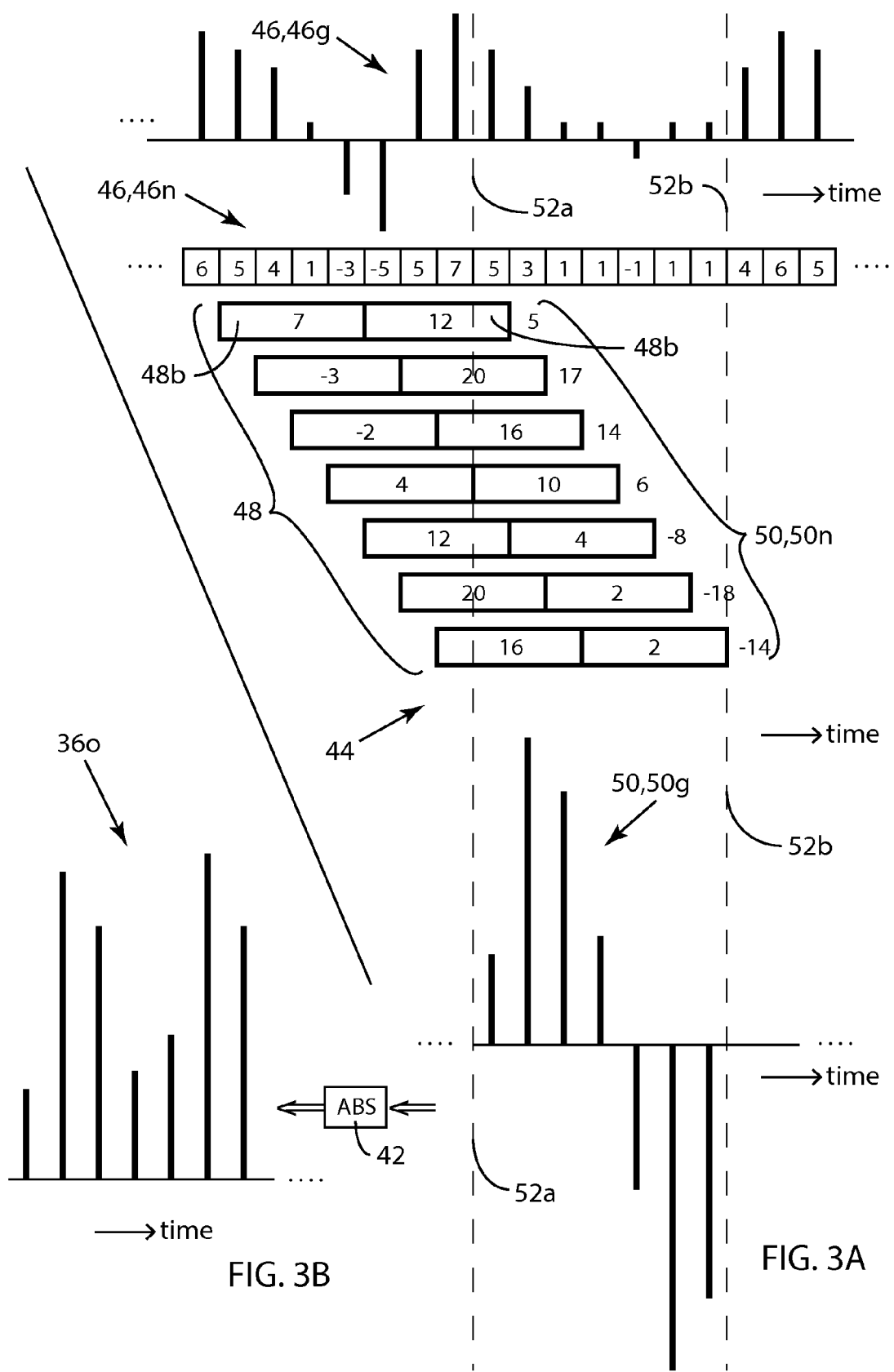
FIG. 3A is an illustration of the operation of the filtering which occurs by applying two differenced sequential boxcar filters to a digitized signal.
FIG. 3B depicts the absolute value of the output signal of the filtering operation illustrated in FIG. 3A.

FIGS. 2, 3A and 3B illustrate an embodiment of a portion of the steps of the inventive method further detailed in FIGS. 4A-11C. FIG. 2 is a schematic block diagram illustrating detailed steps within embodiment 10 by which a selected digitized MCCE channel signal 36i is filtered to generate a corresponding absolute-value velocity signal 36o. The steps of FIG. 2 are applied to various signals within embodiment 10 of the inventive method, as indicated later in the description below.

In FIG. 2, the combined steps, low-pass filter 38, first-difference filter 40, and absolute-value filter 42, are together shown as an absolute-value velocity filter 34. The first two steps of absolute-value velocity filter 34, low-pass filter 38 and first-difference filter 40, are together shown as a bandpass filter 44 which generates a filtered velocity signal 41 of an input signal.

As shown in FIG. 2, an input signal 36i is a 6-second preset time window (epoch) of digitized data from a selected MCCE signal. Low-pass filter 38 operates on input signal 36i followed by first-difference filter 40, and together these two filters generate a digital stream of data 41 which corresponds to the filtered velocity (first derivative) of input signal 36i with certain low and high frequencies filtered out. That is, filter 44 is a bandpass filter. Absolute-value filter 42 simply applies an absolute-value operation (rectification) to filtered velocity signal 41 from first-difference filter 40 to generate output signal 36o which is an absolute-value velocity signal of input signal 36i.

One embodiment of applying a combination 44 of low-pass filter 38 and first-difference filter 40 to a digitized signal is what is called herein "two differenced sequential boxcar filters," and such filtering embodiment is illustrated in FIG. 3A, in which an example digitized signal 46 is shown both graphically (46g) and numerically (46n). Seven pairs of "boxcars" 48b illustrate the sequential operation of boxcar filter 48.

Referring to FIG. 3A, each pair of boxcars 48b in boxcar filter 48 is four time samples in length, and two boxcars 48b are such that one follows the other immediately in time. (Only two of the 14 boxcars 48b are labeled.) The sum of the four time samples of digitized signal 46 in each boxcar 48b is calculated. Thus, for example, the left boxcar 48b of the uppermost (first in time) pair as shown holds the sum of the four time samples it subtends, and the right boxcar 48b of this pair holds the sum of the four time samples it subtends. These two sums are 7 and 12, respectively, and the difference between the right boxcar value and the left boxcar value is 12−7=5. This differenced value 5 is shown to the right of the uppermost boxcar 48b pair, and seven such values, indicated by reference number 50, are shown to the right of the seven example sequential boxcar 48b pairs. This output signal 50 is shown both numerically as 50*n* and graphically as 50*g*. Filter output signal 50 is shown for the seven time samples between the dotted lines labeled 52*a* and 52*b*.

In the example of FIG. 3A, each boxcar 48*b* has a boxcar-width $w_B$ of four samples. The value of $w_B$ determines the frequency response of boxcar filter 48, or the amount of smoothing provided by boxcar filter 48. Larger values of $w_B$ produce a lower central frequency of boxcar filter 48 and therefore more smoothing of the signal on which it operates. Such relationships are well-known to people skilled in the art of digital filtering. Any specific value for $w_B$ used herein is not intended to be limiting. However, for the embodiments exemplified herein, it has been found that values of $w_B$ of around 4 are appropriate for use on intracardiac signals, and values of $w_B$ around 20 are appropriate for ventricular channels. For MCCE signals digitized every 1 millisecond and for sequential four-sample-long boxcar filters 48 ($w_B$=4) illustrated in FIGS. 3A, 3B and 5, the resulting bandpass filter has a center frequency of 125 Hz.

The operation of the two differenced sequential boxcar filters 48 performs low-pass filtering and differentiation to input signal 46 such that filter output 50 is proportional to the velocity of bandpass-filtered digitized signal 46. No scaling has been applied in this example, but such lack of scaling is not intended to limit the meaning of the term two differenced sequential boxcar filters.

FIG. 3B, shown below and to the left of FIG. 3A, simply graphically illustrates the absolute value of output signal 50 as exampled in FIG. 3A. The absolute value of output signal 50 is processed by absolute-value filter 42 as shown in FIGS. 3A and 3B. This absolute-value velocity signal is output signal 36*o* of FIG. 2.

Some steps of the inventive method as illustrated in embodiment 10 include the identification of activations or activity triggers within one or more channel signals of MCCE signals. Activations (activity triggers) are the electrical activity associated with the initiation of the depolarization of the heart muscle cells which occurs during a heart beat, progressing like a wave through the various portions of the cardiac structure and causing the heart to pump.

Figure 4A:
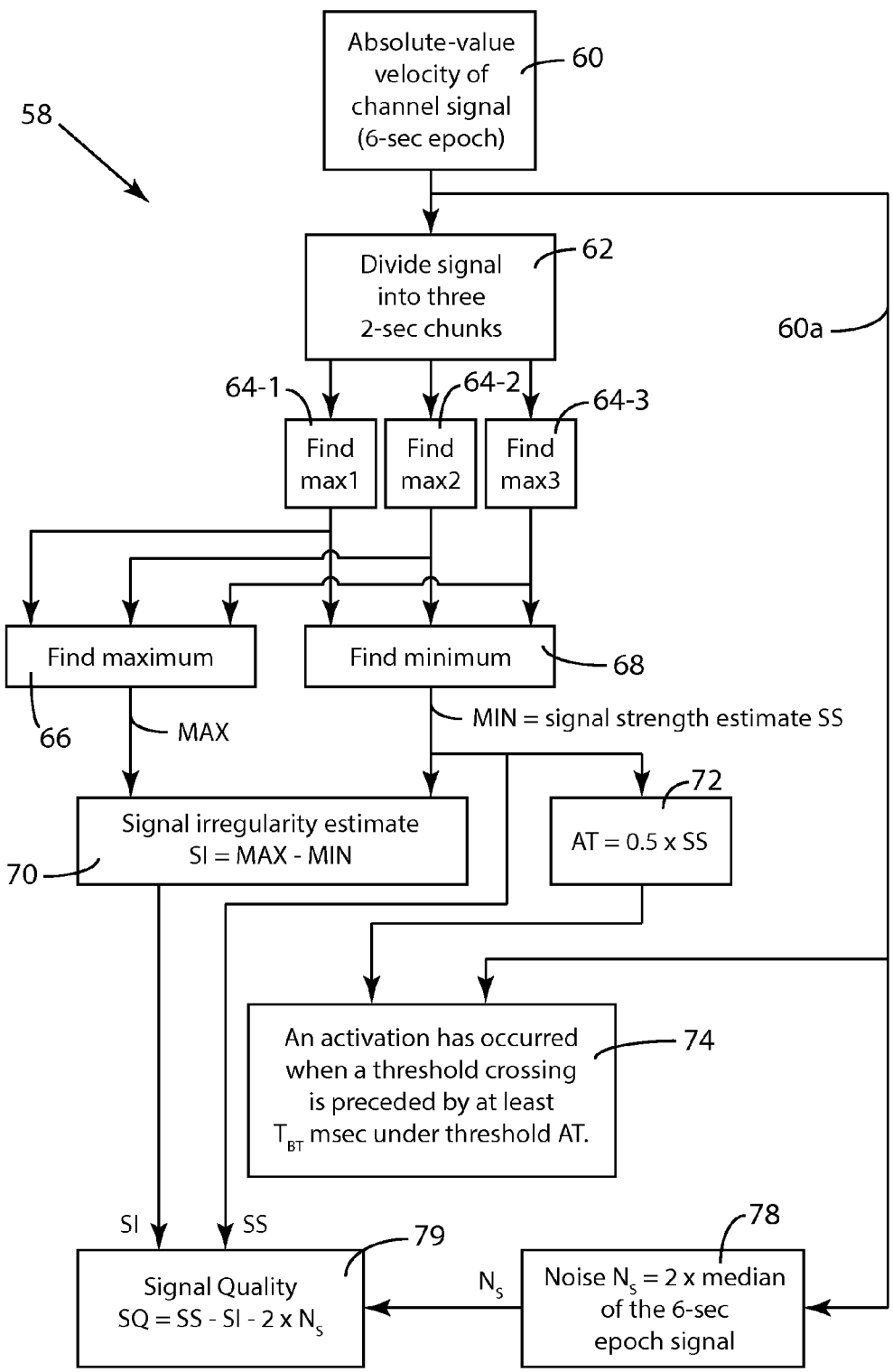
FIG. 4A is a schematic block diagram of the process of determining activations (activity triggers) in the absolute-value velocity signal from an MCCE channel. The steps of this process are applied to more than one channel signal in the inventive method.

FIG. 4A is a schematic block diagram of a process 58 of determining activations (activity triggers) in an absolute-value velocity signal. The steps of process 58 may be applied to more than one channel signal in the inventive method.

In the embodiment of FIG. 4A, a signal 60 which is 6 seconds in duration (6-sec epoch) and is the absolute-value velocity of an MCCE channel signal, is divided into three 2-second "chunks" in method step 62. In method steps 64-1, 64-2 and 64-3, these three chunks are processed to find three signal maxima (max1, max2, and max3), one for each of the three signal chunks. These three values (max1, max2, and max3) are inputs to method step 66 which selects the maximum MAX among the three inputs and method step 68 which selects the minimum MIN among the three inputs. The values MAX and MIN are in turn inputs to method step 70 which determines an estimate SI for signal irregularity. In method step 70, signal irregularity SI is estimated as SI=MAX−MIN. A larger difference between the maximum (MAX) and minimum (MIN) values of the chunk maxima (max1, max2, and max3) indicates that there is more irregularity among the heart beats within epoch 60 being processed. Signal irregularity SI is related to the variations in the "shape" of the activations in MCCE signals while other measurements described later in this document relate to variations in the time of activations.

The value MIN represents an estimate SS of signal strength. SS is multiplied by 0.5 (threshold factor) in method step 72 to determine a value for an activation threshold AT to be used in step 74 to determine the occurrence of activations within the MCCE signal being processed. The value (0.5) of the threshold factor applied in method step 72 of this embodiment is not intended to be limiting. Other values for the threshold factor maybe be applied in embodiments of the inventive method.

Signal irregularity SI and signal strength SS are used in conjunction with an estimate of signal noise $N_S$ to provide an estimate of signal quality SQ in method step 79. In method step 78, signal 60 (provided by flow path 60*a*) is processed to compute its median over the entire 6-second epoch, and such median is multiplied by 2 to produce estimate $N_S$ of signal noise. In method step 78, the calculation of the median of signal 60 may be done using a normal median or a set-member median. For such large data sets (e.g.; 6 seconds at 1,000 samples per second), it has been found that using the set-member median is computationally convenient and highly suitable. In step 79, signal quality SQ is computed as SQ=SS−SI−2$N_S$.

The factor of 2 applied in method step 78 and the factor of 2 applied in method step 79 are both not intended to be limiting. Other values for such factors may be used. The size of the factor in step 78 is related to ensuring that the estimate of noise $N_S$ in signal 60 is a good representation of the noise level in signal 60. The size of the factor in step 79 is related to the relative weight given to noise estimate $N_S$ compared to those given to signal strength SS and signal irregularity SI in generating the estimate for signal quality SQ. The values of 2 for both of these factors have been found to provide good performance for estimating noise $N_S$ and signal quality SQ.

Figure 4B:
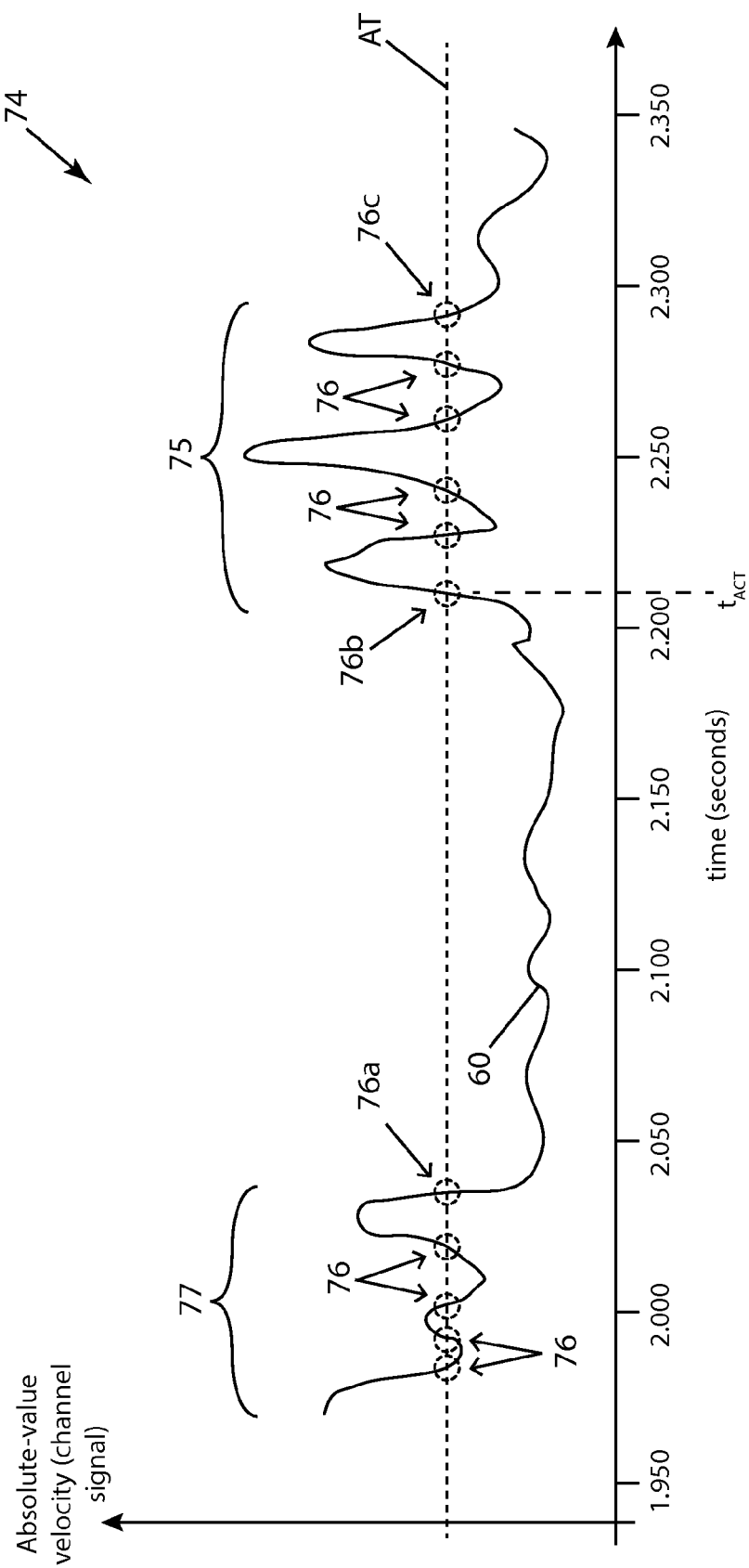
FIG. 4B illustrates the process of identifying activations in an example absolute-value velocity channel signal as processed by the process of FIG. 4A.

FIG. 4B illustrates method step 74 of FIG. 4A, the process of identifying activations in an example absolute-value velocity channel signal 60 as processed by the method steps of FIG. 4A. The signal of epoch 60 being processed is an input to method step 74 as indicated by the signal flow path 60*a*. A portion of example epoch 60 is illustrated in FIG. 4B. Activation threshold AT is shown as a dotted line AT parallel to the time axis and intersecting signal 60 at points 76. (Eleven signal crossings are shown; one such point is labeled 76*a*, one is labeled 76*b*, and one is labeled 76*c*).

As indicated in method step 74 of FIG. 4A, activations in epoch 60 being processed are indicated by identifying threshold crossings 76 before which signal 60 does not cross activation threshold AT for at least $T_{BT}$ milliseconds. The value of before-threshold time $T_{BT}$ chosen may vary according to the type of MCCE signal 60 being processed. For example, it has been found that $T_{BT}$=120 msec is an appropriate value when a ventricular channel is being analyzed, and that $T_{BT}$=90 msec is an appropriate value when an intracardiac channel is being analyzed. These values for $T_{BT}$ are not intended to be limiting; the selection of a value for $T_{BT}$ is based on choosing a value by which a reliable differentiation between subsequent activations and among threshold crossings 76 within an individual activation can be achieved.

In the example of FIG. 4B, the activation labeled 75 shown includes six threshold crossings 76 as indicated by dotted circles occurring in rapid succession, the first being threshold crossing 76*b* and the last being threshold crossing 76*c*. A portion of a previous activation 77 within signal 60 is also shown in FIG. 4B. In activation 77, five threshold crossings 76 occur in rapid succession, the last of which is labeled 76*a*.

The time difference between threshold crossing 76*a* associated with activation 77 and threshold crossing 76*b* associated with activation 75 is about 185 msec as shown in FIG. 4B. In this example, 185 msec is longer than either of the example values for $T_{BT}$; thus threshold crossing 76*b* is determined to be the leading edge of activation 75, and the time at which threshold crossing 76b occurs is determined to be activation time $t_{ACT}$. In this example, threshold 76b is the only such threshold crossing illustrated in FIG. 4B.

Figure 5:
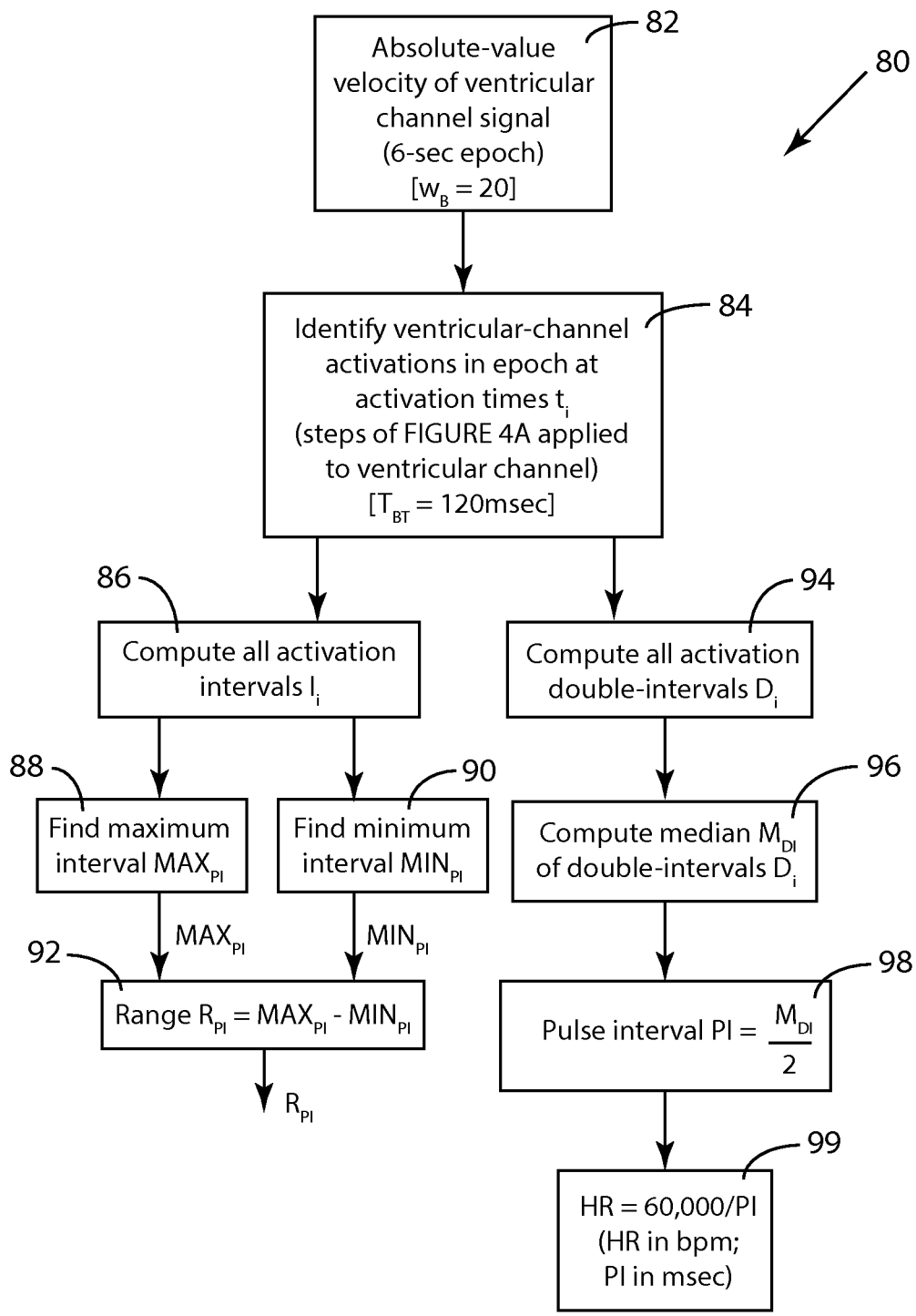
FIG. 5 is a schematic block diagram of the process of determining the ventricular-channel cycle length, herein called "pulse interval" when associated with a ventricular channel.

FIG. 5 is a schematic block diagram of an embodiment 80 of a process of determining the ventricular-channel pulse interval (heart rate). In the inventive automatic method of measuring parameters of MCCE signals, ventricular-channel pulse interval information is used in the calculations to determine intracardiac-channel parameter calculations. The steps of embodiment 80 of FIG. 5 analyze an absolute-value velocity ventricular-channel signal epoch 82, again 6 seconds in duration. In method step 84, activations within epoch 82 are identified by applying steps 58 as illustrated in FIG. 4A. As indicated in method steps 82 and 84, when processing a ventricular channel, values for boxcar-width $w_B$ and before-threshold time $T_{BT}$ may differ from those used for intracardiac channels. In the embodiment of FIG. 5, these values are $w_B=20$ and $T_{BT}=120$ msec.

Activations identified in method step 84 each have an activation time $t_i$, and for purposes of description, there are n such activation times. In method step 86, all activation intervals $I_i$ are computed. There are n−1 activation intervals $I_i$ computed as follows:

$$I_1 = t_2 - t_1$$

.

$$I_i = t_{i+1} - t_i$$

.

$$I_{n-1} = t_n - t_{n-1}$$

In method step 88, a maximum interval $MAX_{PI}$ of the n−1 activation intervals $I_i$ is computed, and in step 90, the minimum interval $MIN_{PI}$ of the n−1 activation intervals $I_i$ is computed. In method step 92, a range $R_{PI}$ for activation intervals $I_i$ is computed as the difference between $MAX_{PI}$ and $MIN_{PI}$.

The n activation times $t_i$ are also used in method step 94 to compute all double-intervals $D_i$ of ventricular-channel signal epoch 82. There are n−2 double-intervals $D_i$, and such double-intervals $D_i$ are computed as follows:

$$D_1 = t_3 - t_1$$

.

$$D_i = t_{i+2} - t_i$$

.

$$D_{n-2} = t_n - t_{n-2}$$

In method step 96, the normal median $M_{DI}$ of all double-intervals $D_i$ is computed, and in step 98, the estimate PI of ventricular-channel pulse interval is computed as $$PI = M_{DI}/2$$

Thus, method steps of process 80 generate an estimate of ventricular pulse interval PI and provide an estimate of the range $R_{PI}$ over which ventricular pulse interval PI varies. The value of pulse interval PI is used in the determination of reference-channel and mapping-channel cycle lengths and is reported as a heart rate HR for the patient being monitored. Heart rate HR in beats per minute (bpm) is determined in method step 99 from pulse interval PI (in msec). (For computational convenience in step 96, a set-member median calculation may be used in place of the normal median calculation.)

Figure 6A:
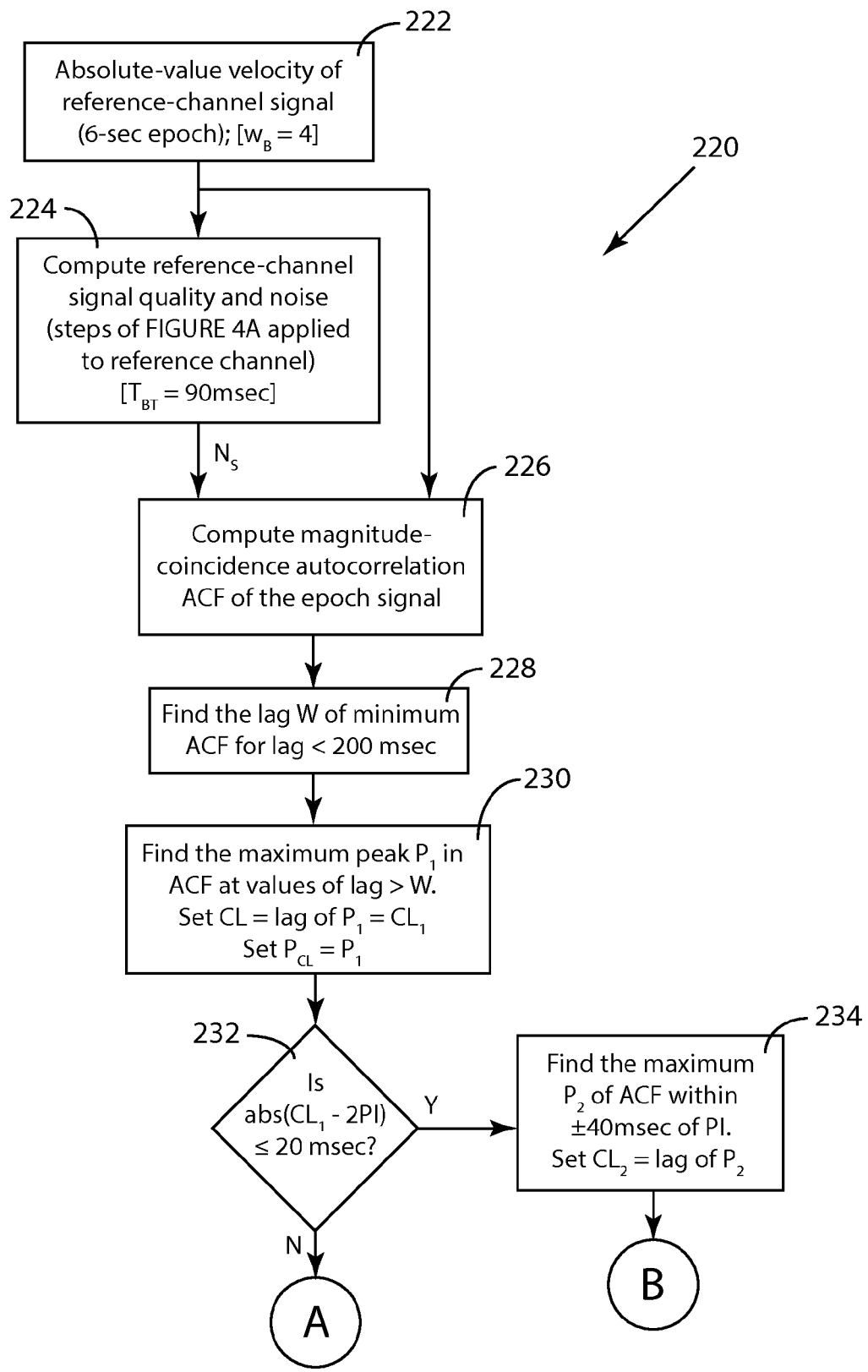
FIGS. 6A and 6B together are a schematic block diagram of the process of determining the reference-channel cycle length in the embodiment of FIG. 1.
Figure 6B:
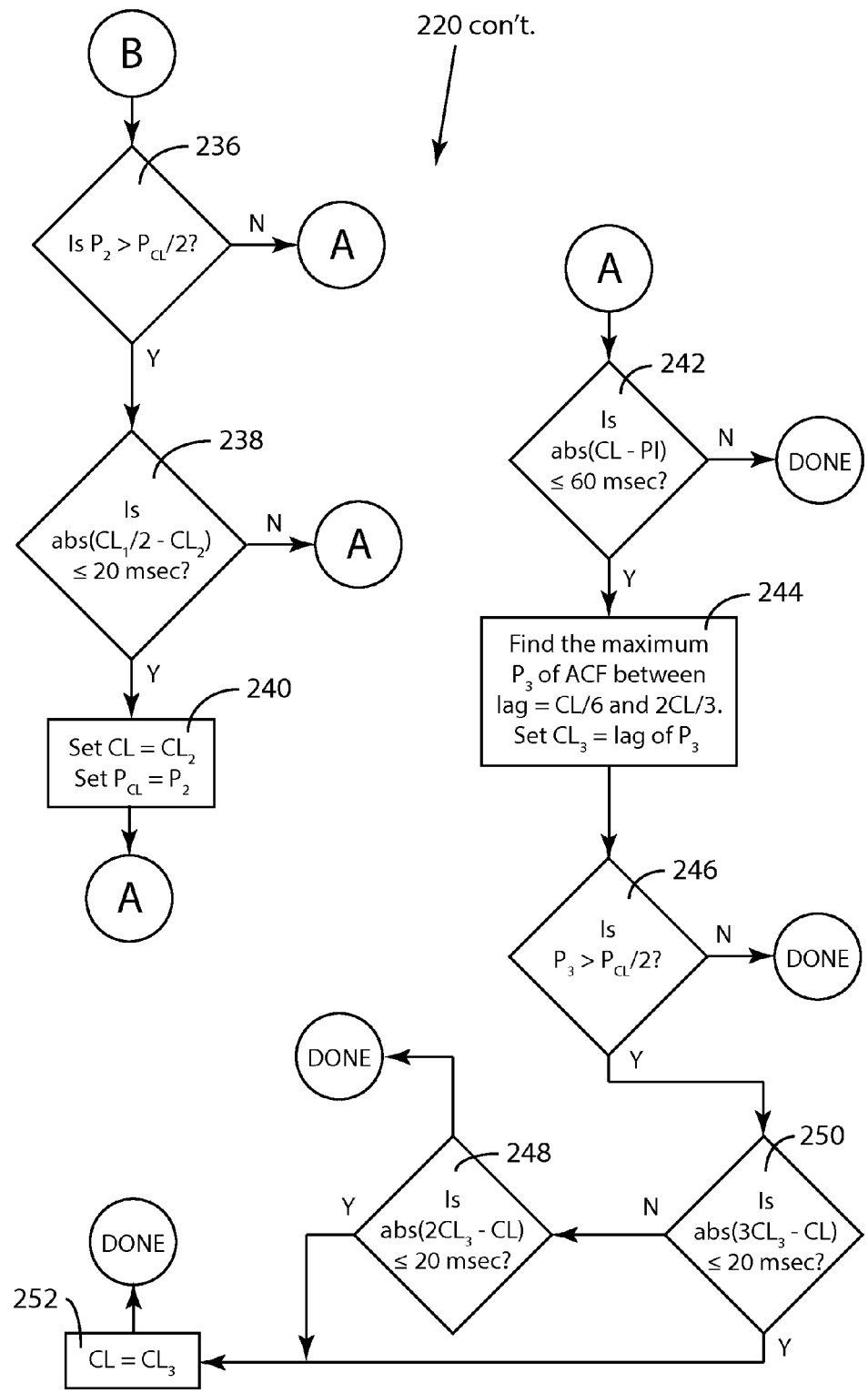

FIGS. 6A and 6B together are a schematic block diagram of a process 220 of determining the reference-channel cycle length CL. (Method step 16 of FIG. 1 includes process 220 along with other elements of the reference-channel cycle-length determination as illustrated in the embodiments of FIGS. 2 through 4B.) The steps of FIGS. 6A and 6B process an absolute-value velocity reference-channel signal epoch 222, again 6 seconds in duration. In step 224, reference-channel signal strength SS, signal irregularity SI, and noise $N_S$ are computed using the steps of FIG. 4A. Method steps 72 and 74 of FIG. 4A are not used in the processing of reference-channel absolute-value velocity signal 222; individual activations within signal 222 are not detected. Signal strength SS, signal irregularity SI, and noise $N_S$ are used to determine signal quality SQ, and noise $N_S$ is used in the computation of the magnitude-coincidence autocorrelation function ACF in method step 226.

In method step 226, a magnitude-coincidence autocorrelation is performed on the data in absolute-value velocity reference-channel signal epoch 222. (The computed autocorrelation function is indicated by the term ACF.) The threshold value for the magnitude-coincidence autocorrelation is dependent on noise $N_S$ in signal 222 as described in the summary section above which defines magnitude-coincidence autocorrelation. As applied in method step 226, the value of the threshold $T_{AC}$ is set to ensure that the thresholding process selects events which are significant events within input signal 222. In one embodiment, $$T_{AC} = 2 \cdot N_S \text{ where noise } N_S = 2 \cdot (\text{median(input)} + 1).$$

The "1" is added to the median for computational convenience and to avoid singular conditions within the system. Values other than 1 may be used and other ways to set threshold $T_{AC}$ may be used; this specific expression for $T_{AC}$ is not intended to limit the scope of this invention.

The remaining method steps of process embodiment 220 in FIGS. 6A and 6B, steps 228-252, encompass analysis of ACF to determine reference-channel cycle length CL. As described above, ACF is a function of lag, and in this analysis, values of lag in ACF are analyzed with respect to ventricular-channel pulse interval PI such that reference-channel cycle-length CL is determined in process 220 based on estimates of pulse interval PI.

In method step 228, a minimum of ACF at values of lag less than about 200 msec is identified. (200 msec is a preset lag threshold.) The lag at this minimum in ACF is labeled W and is an estimate of activity width. The lag threshold value of 200 msec for searching for activity width is chosen such that the width of activations expected for most intracardiac-channel signals will be found at lag values less than 200 msec. The search window (preset lag threshold) should be shorter than the shortest expected value of reference-channel cycle length and longer than the width of activations in the reference-channel signal. Since activations typically are significantly shorter than CL, it is straightforward to set the range to an appropriate value. 200 msec has been found to be a useful value. However, the specific value of 200 msec for the preset lag threshold is not intended to be limiting.

In method step 230, the maximum peak $P_1$ is found in ACF for values of lag greater than W; CL is set at the value of lag $CL_1$ where ACF has its maximum peak $P_1$ for lag greater than W; and an interim peak amplitude $P_{CL}$ is set to P1. ($P_{CL}$, $P_1$, $P_2$, $P_3$, $CL_1$, $CL_2$ and $CL_3$ are interim values in the steps of process 220.) Then in method step 232, if $CL_1$ is very near (within ±20 msec) double the ventricular pulse interval PI, then process 220 proceeds to method step 234. If $CL_1$ is not very near 2PI, then process 220 proceeds to method step 242 in FIG. 6B. (Points A and B in process 220 represent common points joining FIGS. 6A and 6B.) The situation of $CL_1$ being very near double the ventricular pulse interval PI may occur in a condition in which a slight alternation of ventricular pulse interval PI in a pattern of bigeminy (long, short, long, short, etc.) causes the autocorrelation to be slightly stronger at the repeating double interval. Consecutive single intervals are only slightly different, but magnitude-coincidence autocorrelation is very sensitive to the slight timing differences.

Throughout process embodiment 220 of determining reference-channel cycle length CL, there are several time intervals which are used to identify certain values in ACF such as the ±20 msec "nearness" criterion in method step 232. These occur in method steps 232, 234, 238, 242, 248, and 250. In each such occurrence, these specific values have been found to perform well in the embodiment of process 220. (The "nearness" criteria are also referred to as lag intervals. The lag intervals in the method steps of process 220 are: step 232, a first lag interval; step 234, a second lag interval; step 238, a third lag interval; step 242, a fourth lag interval; and steps 248 and 250, a fifth lag interval.)

In method step 234, the maximum amplitude $P_2$ of ACF is identified within a lag interval of ±40 msec of ventricular pulse interval $P_1$, $CL_2$ is set to the value of lag at maximum $P_2$, and process 220 proceeds to method step 236. In method step 236, if the amplitude $P_2$ is greater than half of peak amplitude $P_{CL}$ and if, in method step 238, $CL_2$ is within 20 msec of $CL_1/2$, then in method step 240, CL is set to $CL_2$ $P_{CL}$ is set to $P_2$, and process 220 proceeds to step 242. If both of these two conditions (in steps 236 and 238) are not true, process 220 proceeds to step 242 without setting CL to $CL_2$ and $P_{CL}$ to $P_2$. Method step 238 distinguishes peak $P_2$ from a maximum on one of the boundaries of the ±40 msec lag interval in method step 234. If the $P_2$ is not greater than half of $P_1$, then the process proceeds to method step 242.

In method step 238, if $CL_1/2$ is within 20 msec of $CL_2$, then CL is set to $CL_2$ in method step 240 and the process proceeds to method step 242. If $CL_1/2$ is not within 20 msec of $CL_2$, then the process proceeds to method step 242 without setting CL to $CL_2$.

In method step 242, if CL (set in method step 230 or method step 240) is within 60 msec of ventricular pulse interval PI, then process 220 proceeds to method step 244. If CL is not within 60 msec of PI, then the process ends and the reference-channel cycle length is either CL=$CL_1$ as set in method step 230 or $CL_2$ as set in method step 240.

In method step 244, the maximum amplitude $P_3$ of ACF is identified within the lag interval between lag=CL/6 and lag=2CL/3, interim value $CL_3$ is set to the lag at maximum $P_3$, and process 220 proceeds to method step 246. In method step 246, if amplitude $P_3$ is greater than half of the amplitude $P_{CL}$ at CL (CL is either the lag $CL_1$ at peak $P_1$ or the lag $CL_2$ at peak $P_2$), then process 220 proceeds to method steps 248 and 250. If the amplitude $P_3$ does not satisfy the criterion in method step 246, then process 220 ends and the value of reference-channel cycle length CL is either CL=$CL_1$ as set in method step 230 or $CL_2$ as set in method step 240.

It is possible that there may be a significant peak in ACF between lag=CL/6 and lag=2CL/3. Method steps 248 and 250 are parallel steps which, if either of the criteria in these steps is satisfied, process 220 proceeds to method step 252 in which the reference-channel cycle length CL is set to CL=$CL_3$ and process 220 ends. If neither of these two criteria is satisfied, process 220 ends and reference-channel cycle length CL is either CL=$CL_1$ as set in method step 230 or $CL_2$ as set in method step 240. The criteria in method steps 248 and 250 check whether peak $P_3$ has a value of lag wherein CL is within 20 msec of either $2CL_3$ or $3CL_3$. If either condition is true, then, as stated above, reference-channel cycle length CL is set to $CL_3$ and process 220 ends. The situation of a proper reference-channel cycle length CL being at ⅓ or ½ of ventricular pulse interval PI is related to 3:1 or 2:1 atrio-ventricular conduction with the artificial enhancement of the ACF peak at pulse interval PI because of the ventricular artifact that occurs for some of the atrial activations.

The methods just described can be summarized as three distinct and separable strategies. First is the use of the autocorrelation function to identify repeating cycles in the cardiac rhythm with maximum use of all the data available and little dependance on shape, no dependance on threshold-crossing jitter, and robust to occasional noise glitches. The second important strategy is avoiding the choice of a false cycle length at twice the ventricular pulse interval because the ventricular response slightly alternates in a pattern of bigeminal timing. The third important strategy is avoiding the choice of a cycle length equal to the ventricular pulse interval because ventricular far-field distortions may occur in atrial signals during 2:1 or 3:1 atrio-ventricular conduction. These three strategies are useful separately but more so in combination.

Figure 7A:
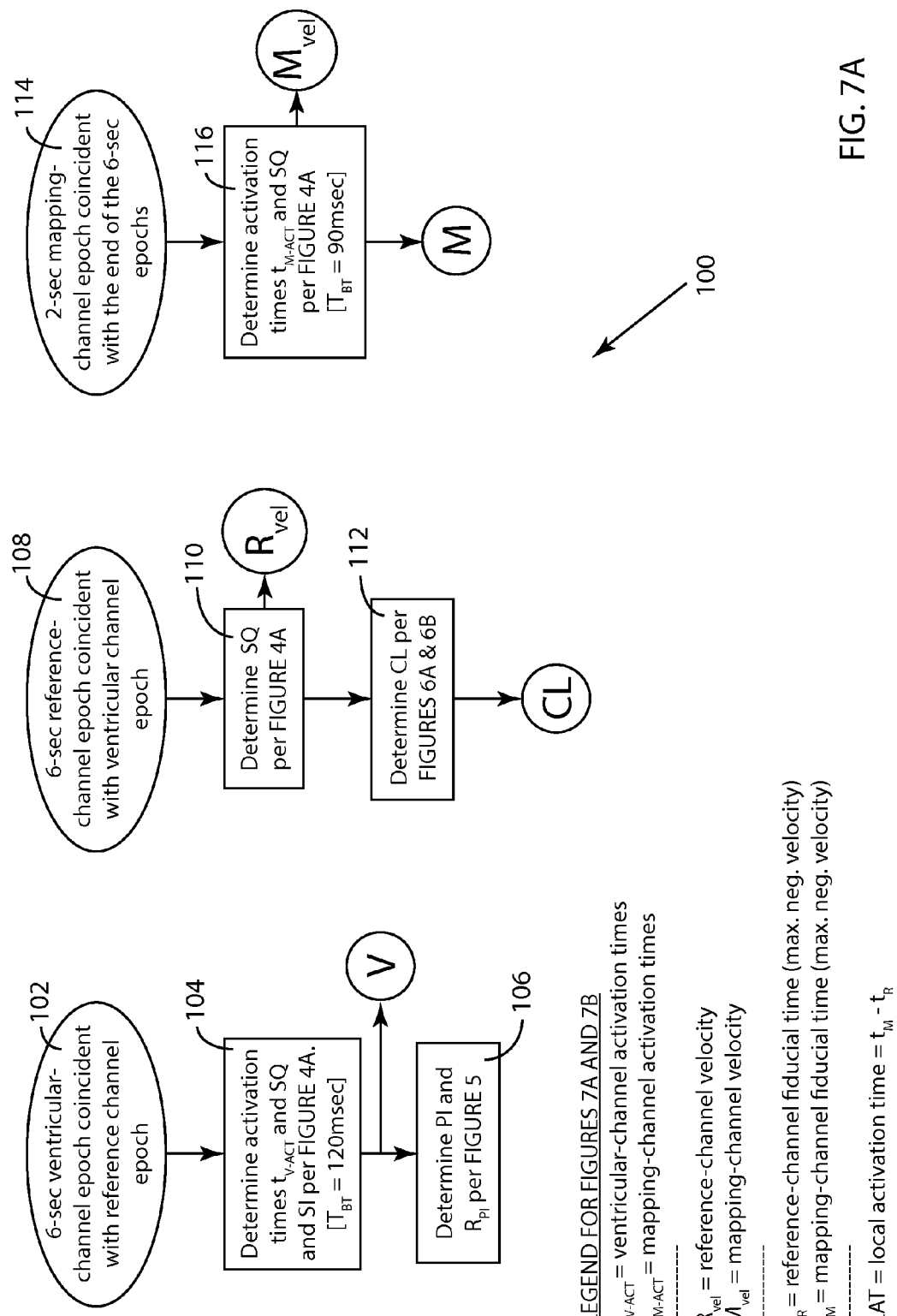
FIGS. 7A and 7B together are a schematic block diagram of the process of determining local activation time (LAT) for a single mapping point in the embodiment of FIG. 1.
Figure 7B:
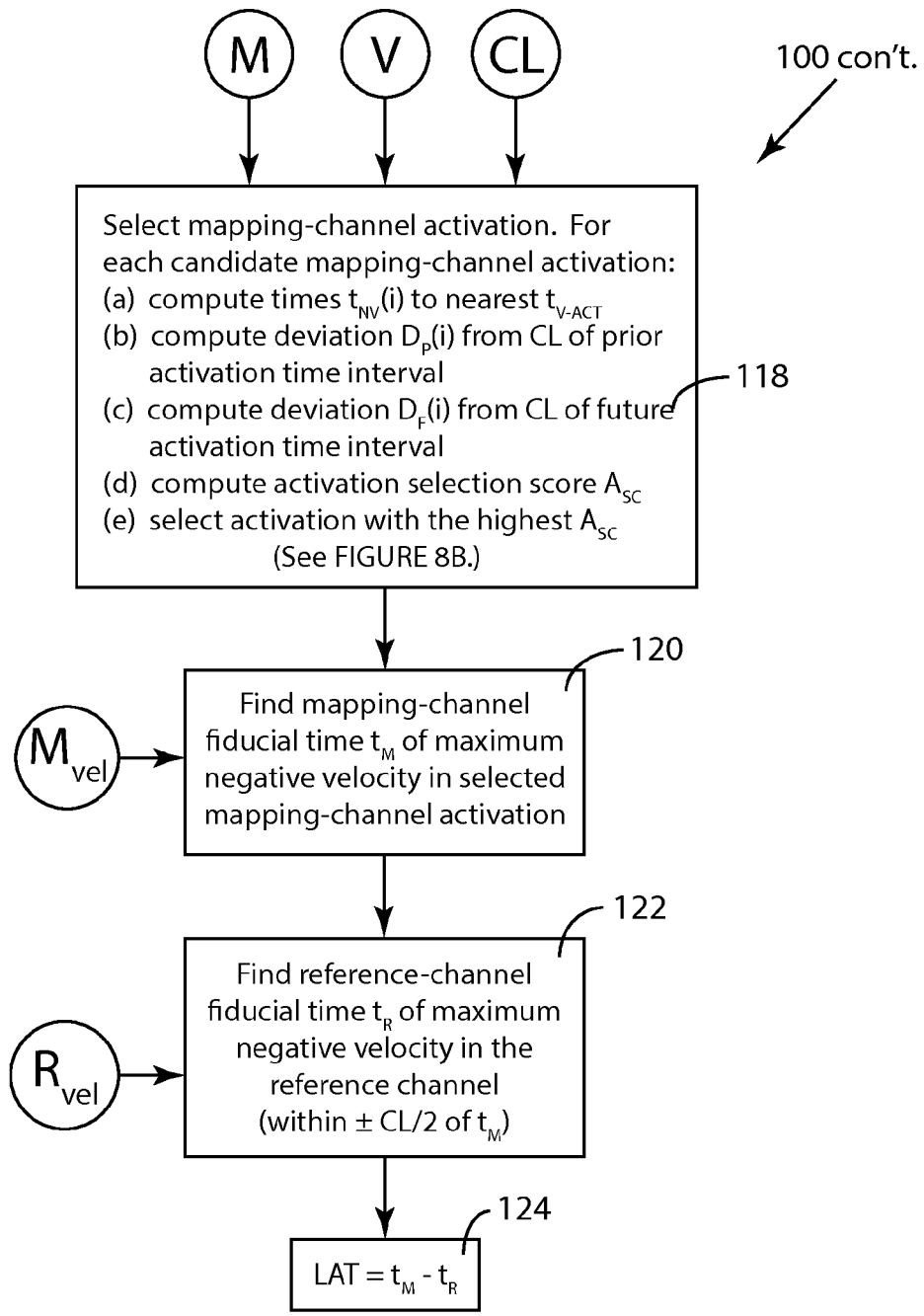

FIGS. 7A and 7B together are a schematic block diagram of an embodiment 100 of the process of determining local activation time (LAT) for a single mapping point in the inventive method of measuring parameters of MCCE signals. FIG. 7A illustrates three MCCE signals (6-sec epochs) on which computations are performed, as has been described above, in order to provide results which are used in the determination of LAT for a single mapping point. A ventricular-channel epoch 102 and a reference-channel epoch 108 are coincident in time, and a mapping-channel 2-sec epoch 114 is coincident with the last 2 seconds of epochs 102 and 108. FIG. 7A includes a legend which defines the terminology used in FIGS. 7A and 7B.

In method step 104, ventricular-channel epoch 102 is processed with the steps of FIG. 4A and produces a set of ventricular-channel activation times $t_{V\text{-}ACT}$ and estimates of signal quality SQ and signal irregularity SI for epoch 102. The ventricular-channel activation times $t_{V\text{-}ACT}$ are used in the determination of LAT as indicated by the circle labeled V which is common with the same such circle in FIG. 7B. In method step 106, ventricular-channel pulse interval PI and range of pulse intervals $R_{PI}$ are computed for presentation to the EP doctor using the steps shown in FIG. 5.

In a similar fashion, in method step 110, reference-channel epoch 108 is processed with the steps of FIG. 4A and produces estimates of signal quality SQ and signal irregularity SI for epoch 108. Within the method steps of FIG. 4A, a velocity signal for the reference channel is computed, and it is used in the determination of LAT as indicated by the circle labeled $R_{vel}$ which is common with the same such circle in FIG. 7B. In method step 112, reference-channel cycle length CL is determined using the steps shown in FIGS. 6A and 6B, and reference-channel cycle length CL is used in the determination of LAT as indicated by the circle labeled CL which is common with the same such circle in FIG. 7B.

In method step 114, mapping-channel epoch 114 is processed with the steps of FIG. 4A and produces a set of mapping-channel activation times $t_{M\text{-}ACT}$ and estimates of signal quality SQ for epoch 114. (Epoch 114 is not sufficiently long to determine a useful estimate of signal irregularity SI. However, if a longer epoch length is used, SI may be estimated in method step 116.) Mapping-channel activation times $t_{M\text{-}ACT}$ are used in the determination of LAT as indicated by the circle labeled M which is common with the same such circle in FIG.

7B. Within the steps of FIG. 4A, a velocity signal for the mapping channel is computed, and it is used in the determination of LAT as indicated by the circle labeled $M_{vel}$ which is common with the same such circle in FIG. 7B.

FIG. 7B shows a continuation of the flow chart of embodiment 100. Inputs to the method steps of FIG. 7B have been computed in the method steps of FIG. 7A, and these inputs are illustrated by the circles labeled as described above. In method step 118, a mapping-channel activation for LAT determination is selected from among the activations and corresponding mapping-channel activation times $t_{M-ACT}$ determined in method step 116. The selection of such activation in step 118 includes the maximization of an activation selection score $A_{SC}$, a value for which is computed for each candidate activation among the set of mapping-channel activations. Details of method step 118 are described later in this document in the discussion of the example of FIGS. 8A and 8B.

After selecting the specific mapping-channel activation to be used to determine LAT in method step 118, a mapping-channel fiducial time $t_M$ is found in method step 120. In determining LAT, a more precise representation of event times is required than the threshold-crossing determination of activation detection in method step 74. In this document, "fiducial time" is the term used to indicate such a more precise determination of an event (activation) time. "Fiducial time" as used herein represents the instant within an MCCE signal at which a depolarization wavefront passes below the positive recording electrode in either a bipolar or unipolar MCCE signal.

As is well-known to those skilled in the field of electrophysiology, one good representation of fiducial time is the instant at which a signal exhibits its maximum negative velocity. Thus, one embodiment of method step 120 includes determining mapping-channel fiducial time $t_M$ as the time at which the maximum negative velocity occurs within the selected activation of the mapping channel. In a similar fashion, a reference-channel fiducial time $t_R$ is found in method step 122. Reference-channel fiducial time $t_R$ is the time at which the maximum negative velocity occurs within ±CL/2 of mapping-channel fiducial time $t_M$.

The use of the time of maximum negative velocity as the fiducial time is not intended to be limiting. Other indications of precise depolarization event times may be used in determining the fiducial times.

In method step 124, the local activation time LAT for a position at which the mapping-channel electrode is located within the heart is computed as LAT=$t_M$-$t_R$. Local activation time LAT is determined relative to the selected reference channel, and values of LAT at a plurality of locations within the region of the heart being mapped are determined during the process of building an LAT map. If the quality of the channel signals being processed degrades before mapping is complete such that mapping cannot be continued, a new map must be generated. Local activation times may be positive or negative times (occurring after or before the corresponding activation event in the reference channel).

Figure 7C:
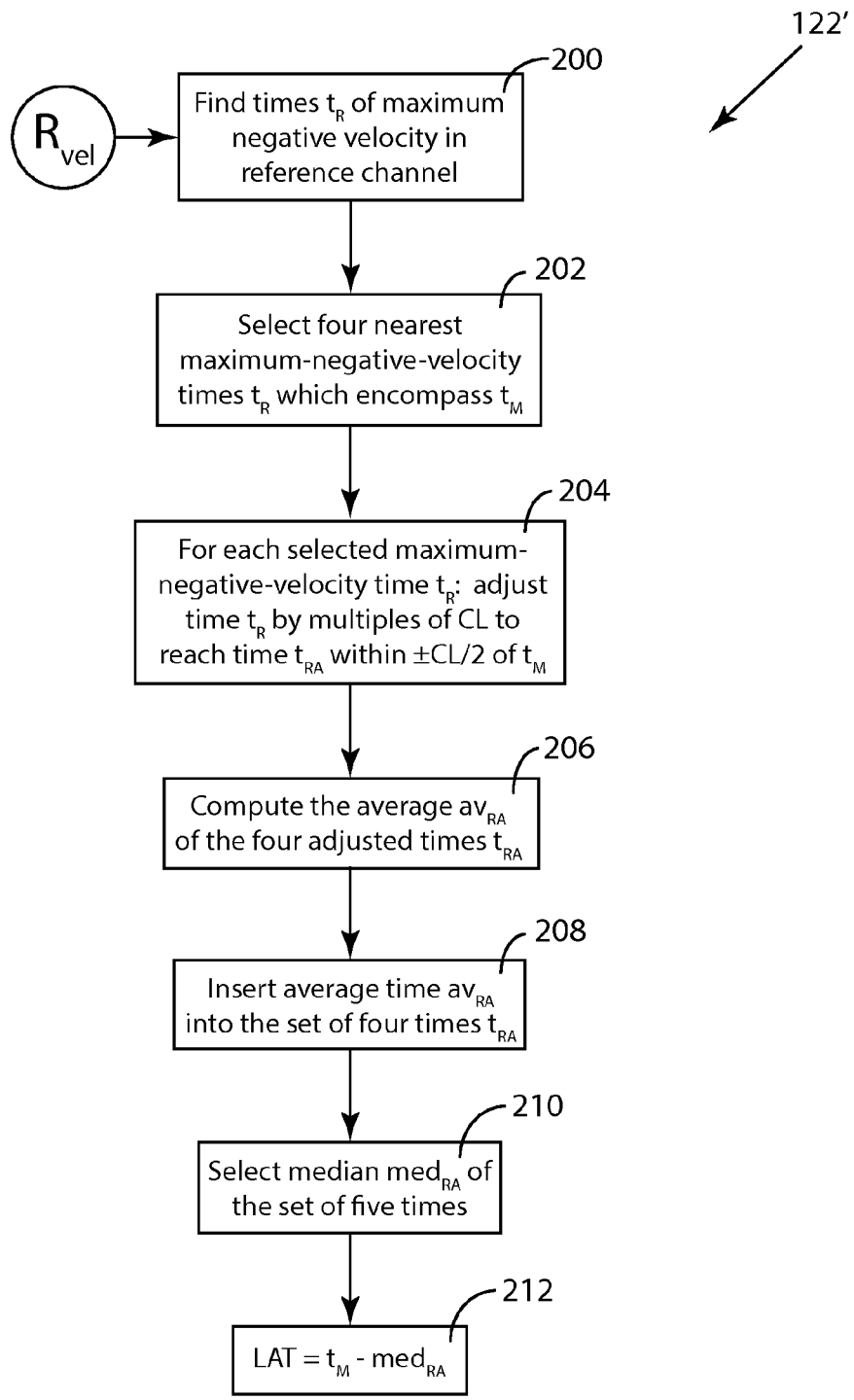
FIG. 7C is schematic block diagram of an alternative embodiment of the inventive method to determine LAT for a single mapping point, using additional fiducial times within a reference-channel signal.

FIG. 7C is a schematic block diagram of an alternative embodiment 122' of the process by which an LAT value is determined for a single mapping point. (Embodiment 122' of FIG. 7C is an alternative embodiment to method steps 122 and 124 of FIG. 7B.) FIG. 7C will be described later in this document, after the example of FIGS. 8A-8D is described.

Figure 8A:
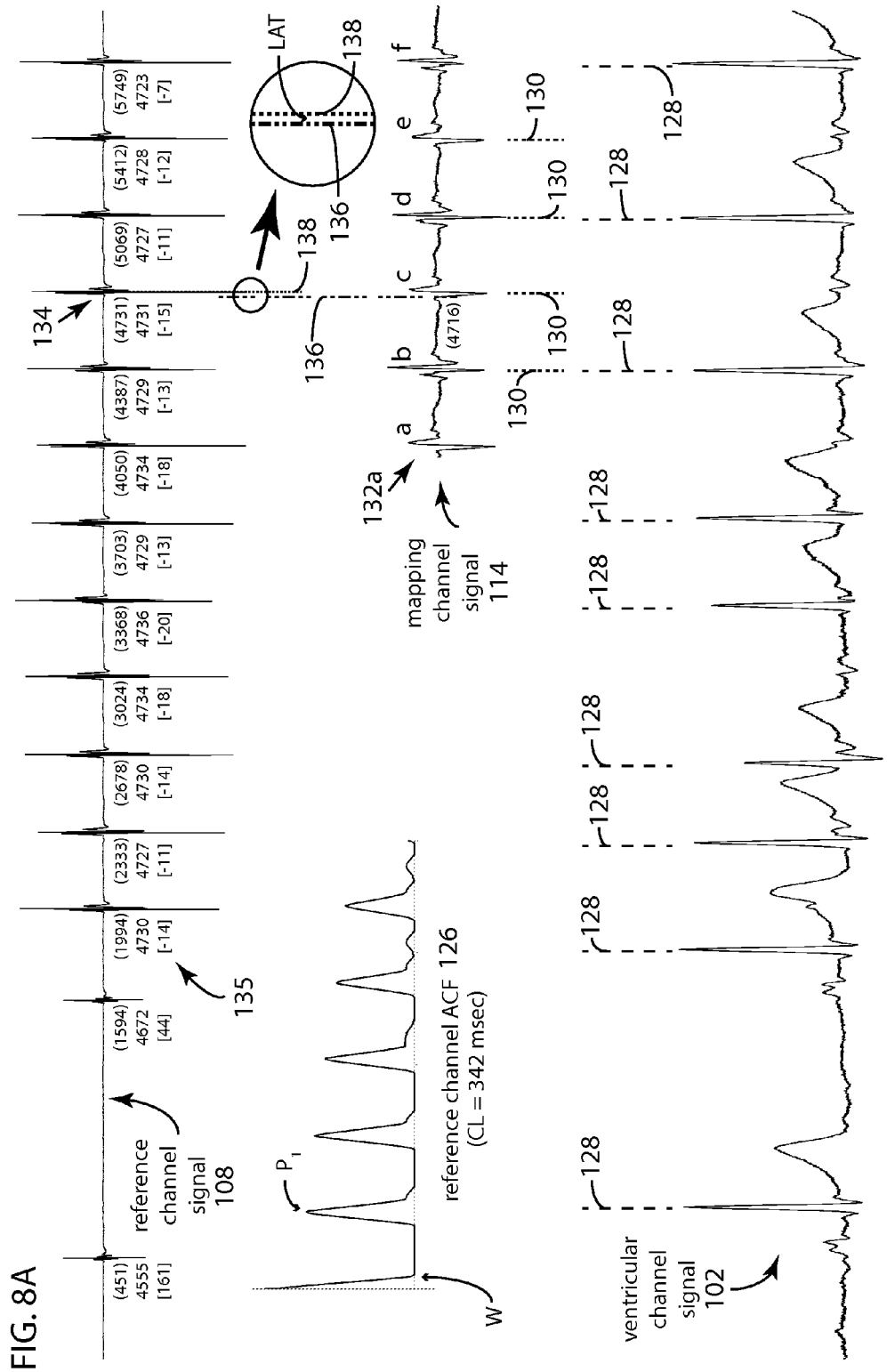
FIG. 8A is a set of MCCE signal plots illustrating an example of the process of determining LAT for a single mapping point as shown in FIGS. 7A and 7B.

FIG. 8A through FIG. 8D together illustrate in more detail the process of determining LAT for a single mapping-channel electrode location. FIG. 8A is a set of exemplary MCCE signal plots. At the top of FIG. 8A is a 6-second epoch of an ECG reference-channel signal 108. At the bottom of FIG. 8A is a 6-second epoch of an ECG ventricular-channel signal 102 time-coincident with reference-channel signal 108. In the middle and to the right of FIG. 8A is a 2-second epoch of an MCCE mapping-channel signal 114 time-coincident with the final 2 seconds of reference-channel signal 108 and ventricular-channel signal 102. (Note that in FIG. 8A, the signal traces illustrated are the MCCE voltage signals, not absolute-value velocity signals which are created during signal processing represented in the steps 100 of FIG. 7A.)

Also illustrated in FIG. 8A is magnitude-coincidence autocorrelation ACF 126 of the absolute-value velocity of reference-channel signal 108. ACF 126 is used to determine reference-channel cycle length CL in a process such as embodiment 220 in FIGS. 6A and 6B. ACF 126 in FIG. 8A is annotated to show activity width W. Peak $P_1$ occurs at a lag value of 342 msec, and the lag at peak $P_1$ is the reference-channel cycle length CL in this example.

Ventricular-channel activations identified in method step 104 are shown in FIG. 8A. Nine such activations, represented by ventricular-channel activation times 128, were identified in ventricular-channel signal 102. In a similar fashion, mapping-channel activation times 130 are shown in FIG. 8A; four mapping-channel activations were identified in method step 116. Note that in this example, the first and last activations in the 2-second epoch of mapping-channel signal 114 were not identified by the threshold-crossing activation detection process of method step 74 of FIG. 4A. (For description purposes, all six activations in mapping-channel signal 114 are labeled 132a through 132f in FIG. 8A even though only four such activation were detected. The number 132 is not repeated with the letters a-f for simplicity in the figure. Activations 132a and 132f were not detected.)

FIG. 8B presents a table detailing method steps 118 by which a specific mapping-channel activation is selected for the determination of LAT for the example of FIG. 8A. FIG. 8B includes a legend further defining the terms utilized in construction of and computations within the table for this example. In method step 112 of FIG. 7A, reference-channel cycle length CL was determined to be 342 milliseconds, shown in FIG. 8B at the top of the table.

As mentioned above, local activation time (LAT) is measured by the time difference between a fiducial time $t_M$ in an activation in the mapping channel and its corresponding fiducial time $t_R$ in the reference channel. As part of this determination, an activation within the mapping-channel signal 114 must be selected for such computation, in method step 118. This selection process includes: (a) for each mapping-channel activation i, determining the time $t_{NV}(i)$ to the nearest ventricular-channel activation for each mapping-channel activation; (b) for each mapping-channel activation i, determining the deviation $D_P(i)$ from CL of the time to the previous mapping-channel activation i−1; and (c) for each mapping-channel activation i, determining the deviation $D_F(i)$ from CL of the time to the next (future) mapping-channel activation i+1. The mathematical representations of these determinations are shown in the legend of FIG. 8B.

To generate a full map of local activation times, often a large number of individual points must be determined. This can be a time-consuming process. It is therefore desirable to determine each individual value of LAT as quickly as possible once a new position of the mapping-channel electrode being manipulated by the EP doctor is established. It has been found that about 2 seconds is often required to make a good determination. At typical intracardiac heart rates being measured, only a few activations occur in the mapping channel during a 2-second epoch period, so it is helpful to increase the number of candidate activations by adapting to situations where an activation is "missing" due to a failed activation detection or to a simple epoch-end timing situation. The inventive method includes a beginning-of-data rule and an end-of-data rule to increase the number of candidate mapping-channel activations. These special rules are as follows:

Beginning-of-data rule: In some cases, the first detected activity may be very near the beginning of available data. If the expected previous activity to a detected activity would be located before the beginning of the mapping-channel epoch, then there is no evidence that detections failed and the value for $D_P(i)$ for such a candidate activation is presumed to be 0. However, if the amount of time in the available data in the mapping-channel epoch is longer than the expected cycle length CL, then it is likely that an activation failed to be detected due to some kind of noise in the mapping-channel signal, an irregular signal, or an insufficiency in the detection algorithm. In this case, $D_P(i)$ is set to $t_{M-ACT}(i)$–CL, but not less than 0, where CL is the reference-channel cycle length.

End-of-data rule: This rule is symmetrical to the beginning-of-data rule and is created to handle the same available data constraint at the end of the data. $D_F(i)$ for only the last candidate mapping-channel activation is set to 0 if the last detected activity is within one reference-channel cycle length CL of the end of data. However, there may be more time in the available mapping-channel epoch data than one CL after the last detected activation. In this case, it is very likely that some kind of noise in the mapping-channel signal, an irregular signal, or an insufficiency in the detection algorithm caused a failed activation detection. In this case, the value of $D_F(i)$ is set to the length of available following data minus CL or $D_F(i) = t_{ME} - t_{M-ACT}(i) - CL$, but not less than 0, where $t_{ME}$ is the mapping-channel epoch length, in this example, 2000 msec, and CL is the reference-channel cycle length. Two such situations are illustrated in the example of FIGS. 8A and 8B.

The mapping-channel activation which is selected is the activation for which activation selection score $A_{SC}(i)$ is a maximum. As shown in FIG. 8B, $$A_{SC}(i) = t_{NV}(i) - D_P(i) - D_F(i).$$

It is desirable that the selected mapping-channel activation be far in time from a ventricular-channel activation and that the neighboring cycle lengths in the mapping channel be close to reference-channel cycle length CL. This mathematical construction of the activation selection score $A_{SC}(i)$ accomplishes this desired relationship.

The computations outlined above and represented in FIG. 8B were carried out for the four candidate mapping-channel activations 132b through 132e (having activation times labeled 130). The activations labeled 132a and 132f were not detected; activation 132a occurred too close to the beginning of epoch 114, and activation 132f was not large enough to trigger the threshold in activation detection step 74. Thus, as shown FIG. 8B, both the beginning-of-data rule and the end-of-data rule were applied in this example to determine values for activations 132b and 132e. In the row of data in the table for mapping-channel activation 132b, the value of $D_P$=40 was determined by application of the beginning-of-data rule, and in the row of data in the table for mapping-channel activation 132e, the value of $D_F$=247 was determined by application of the end-of-data rule.

Mapping-channel activation 132c is selected based on its maximum activation selection score $A_{SC}$=290 among the candidate mapping-channel activations.

FIGS. 8C-1 through 8C-4 are a set of plots illustrating in detail method steps 120, 122, and 124 in which LAT is computed based on selected mapping-channel activation 132c and a reference-channel activation 134. (Note that reference-channel activation 134 is not detected in the inventive method but it is clear in FIG. 8A that activation 134 is an activation near in time to $t_M$.) As indicated above, in this example, fiducial times $t_M$ and $t_R$ are the instants in the mapping-channel and reference-channel activations at which the maximum negative velocity occurs. FIG. 8C-1 illustrates an expanded signal of mapping-channel activation 132c, and FIG. 8C-3 illustrates an expanded signal of mapping-channel activation velocity 132c:v. Mapping-channel fiducial time $t_M$ is indicated by the dotted line labeled 136. The value of $t_M$ in this example is 4716 msec as indicated to the left of mapping-channel activation 132c in FIG. 8A.

Reference-channel activation 134 is the activation in reference-channel signal 108 which is located within ±CL/2 along the time axis of reference-channel signal 108. FIG. 8C-2 illustrates an expanded signal of reference-channel activation 134, and FIG. 8C-4 illustrates an expanded signal of reference-channel activation velocity 134:v. Reference-channel fiducial time $t_R$, indicated by the dotted line labeled 138, is clearly located within ±171 msec (±CL/2) of $t_M$.

In this example, reference-channel activation 134 occurs after mapping-channel activation 132c, and the local activation time LAT=$t_M - t_R$=–15 msec. This value of LAT provides a single point in the generation of an LAT map. As mentioned above, an LAT map is based a single reference channel with its electrode placed at the same point in the cardiac structure throughout the entire generation of the map. A plurality of LAT measurements is used to generate an LAT map, each such point being made available for display by the inventive system.

In FIG. 7C, an alternative embodiment 122' for LAT determination is illustrated. Alternative embodiment 122' takes advantage of the fact that multiple fiducial times $t_R$ are available in reference-channel signal 108 to which mapping-channel fiducial time $t_M$ may be compared. In method step 200, the times $t_R$ of maximum negative velocity generated in method step 110 of FIG. 7A are identified in reference-channel signal 108. (As described above, activations in the reference channel are not detected using a threshold-crossing technique; rather a simple numerical search method may be used to find the times $t_R$ of local relative negative-velocity maxima in signal 108.) In method step 202, the four nearest values $t_R$ to mapping-channel fiducial time $t_M$ are selected from among the values of $t_R$, and in method step 204, each of these four times $t_R$ are adjusted by adding or subtracting multiples of reference-channel cycle length CL until each adjusted value $t_{RA}$ is within ±CL/2 of $t_M$ so that $t_{RA}$ now represents its relative time position within one cycle length CL. In method step 206, these four values are averaged and this average $av_{RA}$ is included with the set of four values of $t_{RA}$ in method step 208, creating a set of five time values. In method step 210, the median $med_{RA}$ of this set is found and in method step 212, LAT is determined as LAT=$t_M - med_{RA}$.

Referring again to FIG. 8A, reference-channel signal 108 is shown with a set of numerical values 135 next to each activation in signal 108. (Only one such triplet 135 of values is labeled with reference number 135 to avoid clutter within FIG. 8A.) There are 14 such triplets 135 of values, and each triplet consists of (1) a fiducial time $t_R$ of the maximum negative velocity in signal 108 (the number in parentheses), (2) the adjusted time $t_{RA}$ by adding or subtracting multiples of cycle length CL to place $t_{RA}$ within ±CL/2 of $t_M$, and (3) the time difference between $t_M$ and $t_{RA}$, also referred to as intermediate LAT values. This set of time values is also shown in the table of FIG. 8D.

Referring to FIG. 8D, rows A, B, and C correspond to the time value triplets described in the above paragraph. Row D is an ordered list of the intermediate LAT values in row C. Due to variations in measurement conditions or sources of variability, outlier values may be present at either end of this ordered list. To avoid such outliers (such as the two highest values in row D, 44 and 161), an interquartile set of values is selected in row E, dropping the lowest and highest 25% of values from the ordered list. This interquartile list may then be used to provide an estimate of a measurement confidence interval for method step 26 in FIG. 1. The range of this interval is indicated by the end values of row E which range from −15 to −11, or a ±2 msec LAT measurement confidence interval. Further, a measurement-confidence criterion for method step 26 in FIG. 1 may be as follows: if the width of the measurement confidence interval (in this example, 4) is greater than some percentage of cycle length CL, then alert the EP doctor in method step 30. This width percentage criterion may be about 5% but this value is not intended to be limiting. An absolute width, say 15 msec, may also be used as the criteria; again such absolute width criterion value is not intended to be limiting.

Referring to FIG. 8D to illustrate the alternative method of LAT determination described in FIG. 7C, the four times $t_R$ indicated by reference number 214 are the four nearest times $t_R$ which encompass mapping-channel fiducial time $t_M$, forming a set 214 of four values $t_R$ (in row A) as described in method step 202. The four values are adjusted as described above and form the set of four values $t_{RA}$ (in row B) described in method step 204. The average of these four values $t_{RA}$ is computed in method step 206 ($av_{RA}$=4730.25 msec), This value $av_{RA}$ is added to set 214 to form a set of five values as indicated in method step 208. The set of five values is now the set (4727, 4729, 4730.25, 4731, 4734). The median $med_{RA}$ of this set is 4730.25 as found in method step 210, and LAT is determined by LAT=$t_M$−$med_{RA}$, or LAT=4716−4730.25=−14.25 msec. One advantage of such an embodiment is that some additional computational precision occurs with the use of the averaging step.

The use of the four nearest times $t_R$ which encompass $t_M$ is not intended to be limiting. Other choices for the number of values $t_R$ used in the LAT determination may be employed.

Additionally, the steps described with respect to FIG. 8D also form a second alternative embodiment for LAT determination, potentially taking into account even more reference-channel fiducial times $t_R$ in the estimate of LAT. In this second alternative embodiment, the median value of the interquartile set of intermediate LAT values may be used as the LAT value for the current mapping point. As shown in FIG. 8D, the median value in row D is −13, the LAT value for this second alternative method of LAT determination. Again as above, other choices may be made for the number of values of $t_R$ used in the determination of LAT.

Signal quality SQ as determined in method step 79 of FIG. 4A is also applicable for use within method step 24 of FIG. 1 in which signal quality is monitored to provide alert 28 when signal quality SQ degrades. One criterion by which to assess signal quality in method step 79 of FIG. 1 is simply to determine if all three signal quality values (ventricular channel, reference channel and mapping channel) are positive. The signal quality SQ determination for the mapping channel differs from that of the other two channels in that it does not include a signal irregularity SI term (i.e., SQ=SS−2$N_S$ for the mapping channel) since the 2-second epoch of the mapping channel is too short to generate a meaningful value for signal irregularity SI. The decision of method step 79 is in the affirmative if any of the three signal quality SQ values is negative, at which time an alert is given to the EP doctor. Other criteria may be used in method step 24 to trigger user alert 20.

As described above, activation maps are used during certain cardiac procedures. But during such procedures, a variety of other cardiac parameters may advantageously displayed. Among these may be: (1) a value for starting reference-channel cycle length; (2) a value for current reference-channel cycle length CL with a confidence interval; (3) a value for LAT with a confidence interval; and (4) a value for ventricular-channel pulse interval PI with a confidence interval. All of these quantities are generated by the inventive method disclosed herein. For example, a confidence interval for current reference-channel cycle length CL may be determined from the lag L2 of a peak in ACF near twice the cycle length CL, with the confidence interval being ±(L2−2CL) interval. A confidence interval for the LAT measurement may be ±half the interquartile range as described above. A confidence interval for ventricular pulse interval PI may be represented by range $R_{PI}$ (±$R_{PI}$/2) as computed in method step 92 of FIG. 5.

As described above, an activation map comprises a plurality of LAT measurements all of which are made relative to a particular reference-channel signal. One aspect of the inventive automatic method of measuring parameters of multi-channel cardiac electrogram signals includes the ability to compensate for signal degradation in the reference channel during the creation of an activation map. Since LAT maps are made relative to a specific reference channel, if the reference-channel signal being used degrades during mapping below a useful level of signal quality, the inventive method enables another reference channel to be selected and recreates the set of LAT measurements based on the new reference channel and generates a new map. This is possible since the inventive method computes reference-channel parameters as described above for several reference channels in real-time and stores the necessary parameters for use if needed. Very fast computation available with present computing equipment enables these "extra" channels to be recorded and analyzed in real-time without hindering the operation of the "current" channels being used to create a map.

Figure 9:
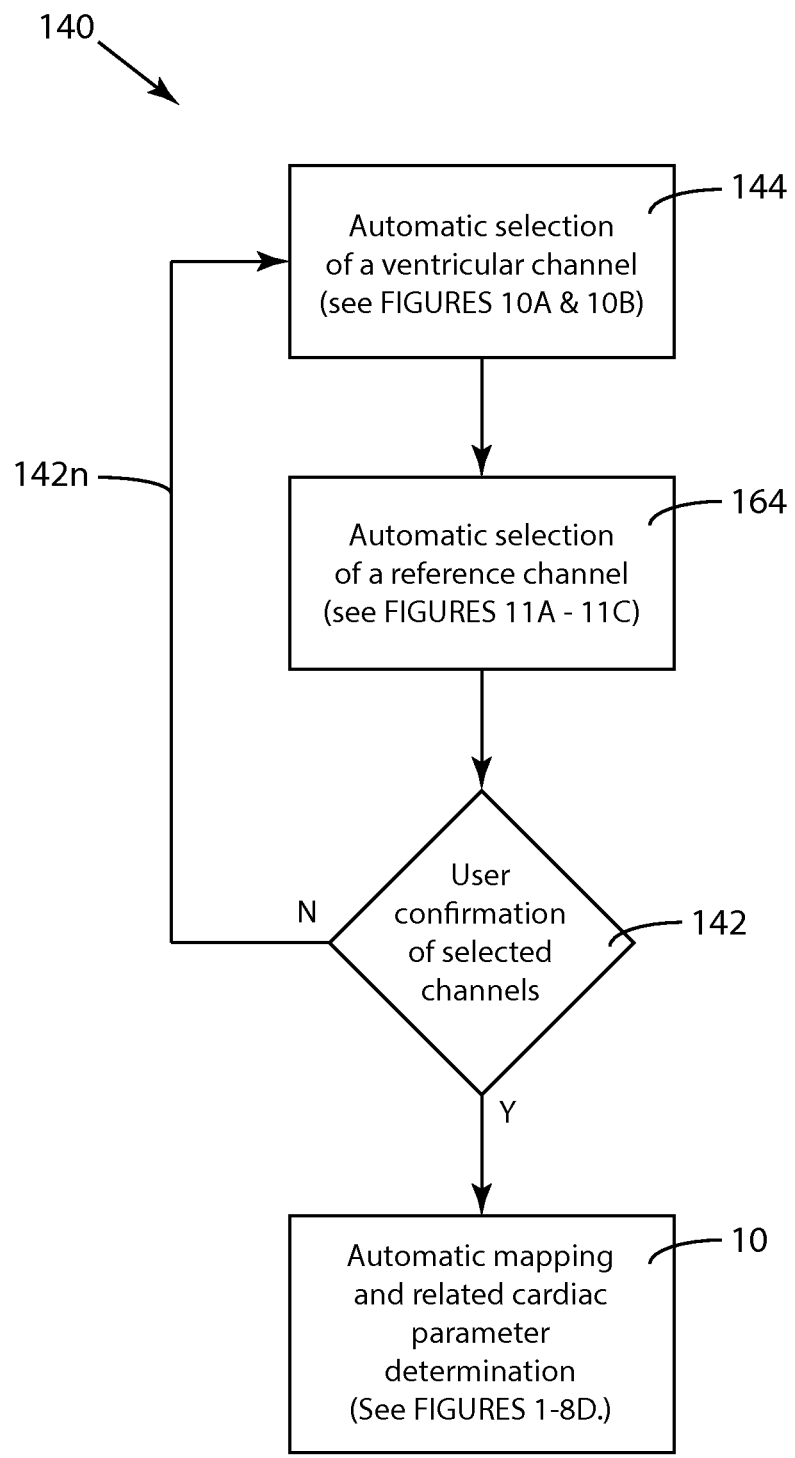
FIG. 9 is a schematic diagram illustrating the inclusion of automatic selection of the ventricular and reference channels in the inventive automatic method of measuring parameters of MCCE signals.

As seen above, a ventricular channel and a reference channel from among the channels of the MCCE signals are used in the automatic method of the present invention. The processes of selecting these channels automatically are among the various aspects of the inventive automatic method. FIG. 9 is a schematic diagram illustrating the inclusion of automatic selection of the ventricular and reference channels to the inventive automatic method of measuring parameters of MCCE signals. The steps of this overall combination are indicated by reference number 140.

Figure 10A:
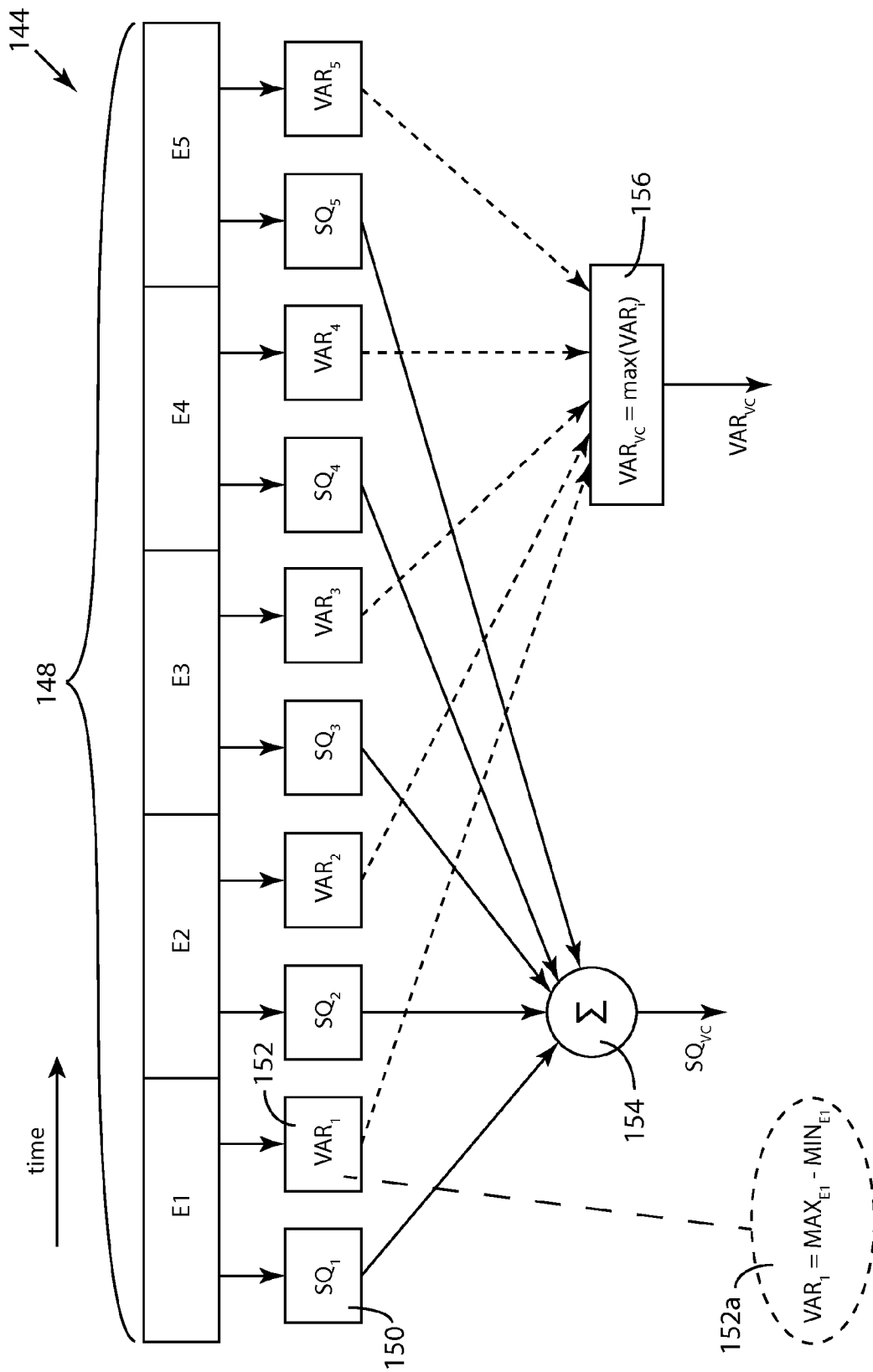
FIG. 10A is a schematic block diagram of the process of automatically selecting a ventricular channel from a set of candidate MCCE channels, specifically illustrating the determination of parameters for a single candidate ventricular channel.
Figure 10B:
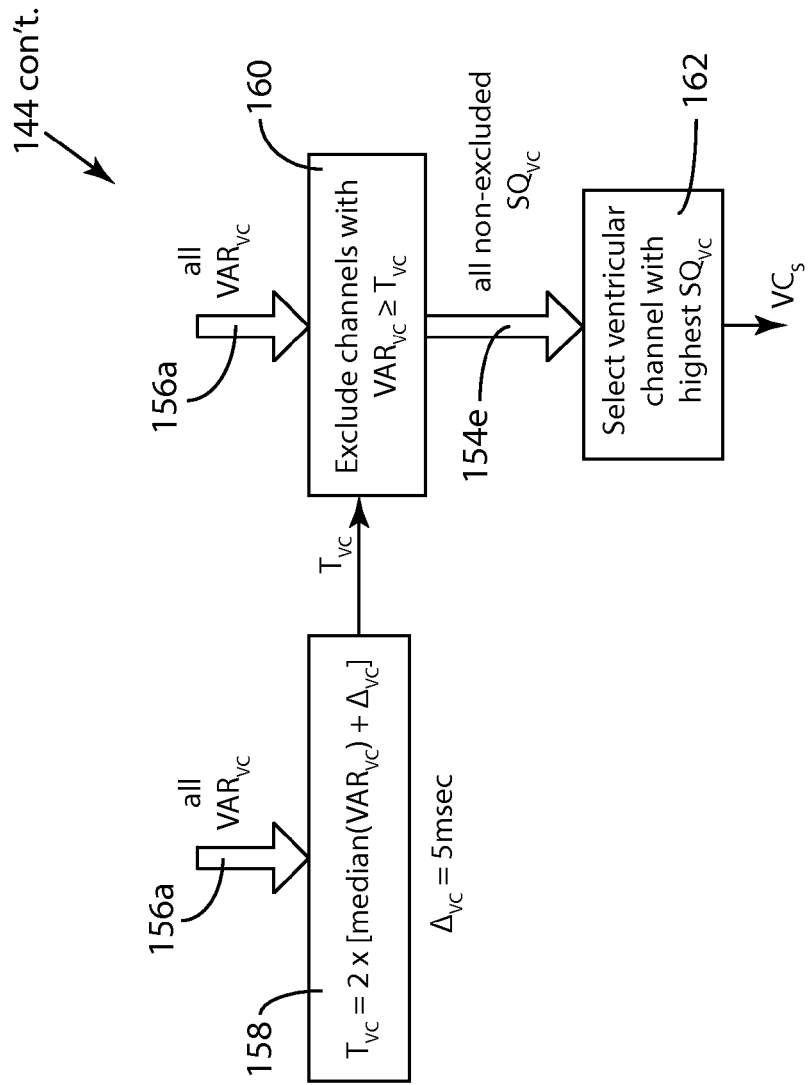
FIG. 10B is a schematic block diagram of the process of automatically selecting a ventricular channel from a set of candidate MCCE channels, specifically illustrating the automatic selection from among candidate ventricular channels which have had parameters determined in the automatic process of FIG. 10A.
Figure 11A:
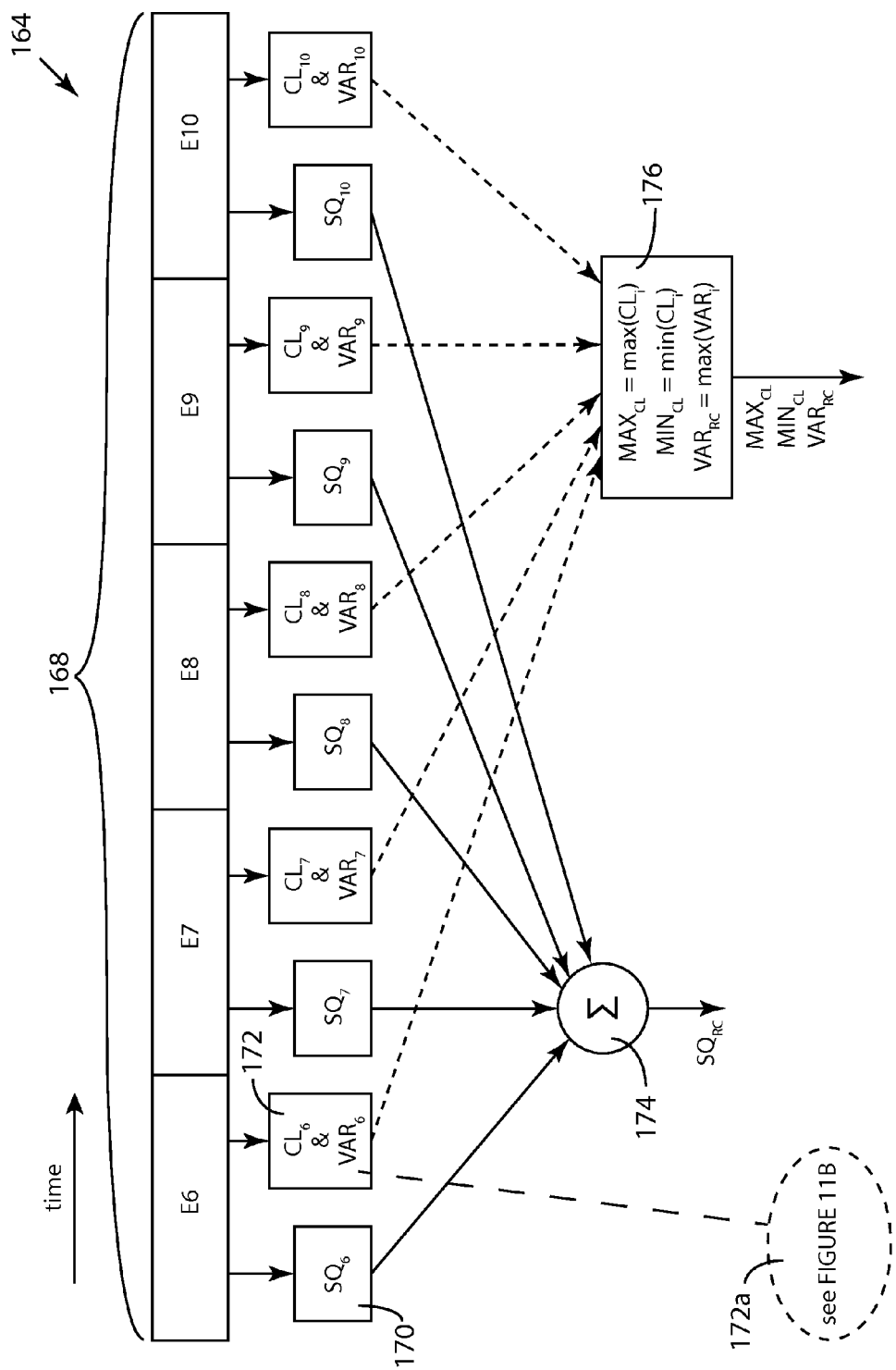
FIG. 11A is a schematic block diagram of the process of automatically selecting a reference channel from a set of candidate MCCE channels, specifically illustrating the determination of parameters for a single candidate reference channel.
Figure 11C:
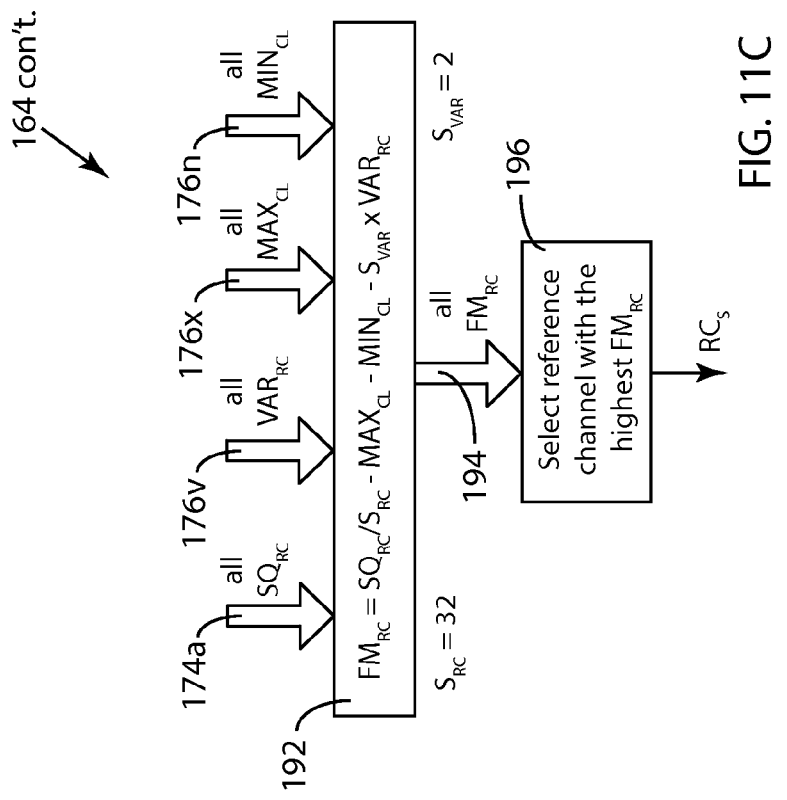
FIG. 11C is a schematic block diagram of the process of automatically selecting a reference channel from a set of candidate MCCE channels, specifically illustrating the automatic selection from among candidate reference channels which have had parameters determined in the automatic process of FIGS. 11A and 11B.
Figure 11B:
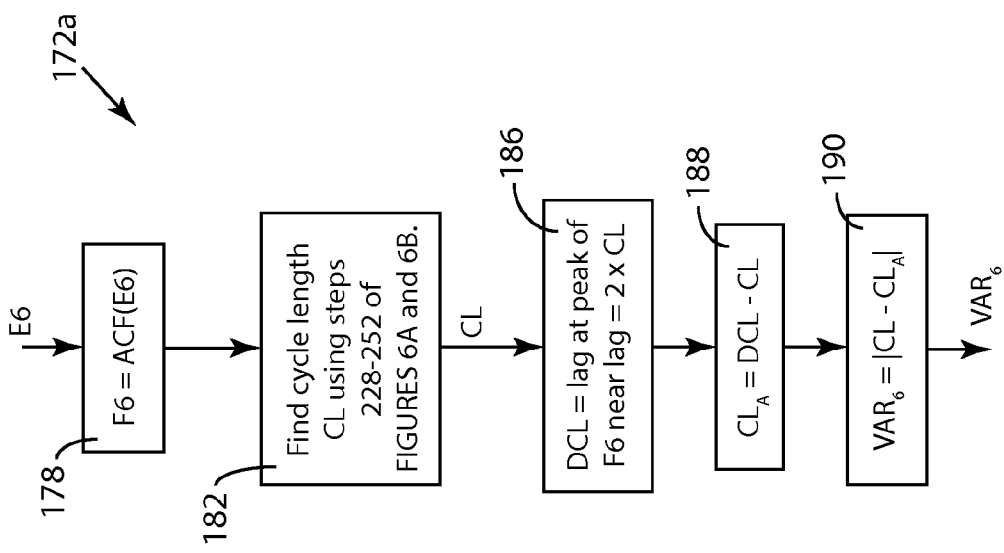
FIG. 11B is a schematic block diagram of the process of automatically determining the variability parameter for a single candidate reference channel as used within the process illustrated in FIG. 11A.

Referring to FIG. 9, these automatic initialization steps include automatic selection of a ventricular channel, indicated by reference number 144. The method steps of an embodiment of automatic process 144 are illustrated in FIGS. 10A and 10B and described in detail below. Following the selection of a ventricular channel, a reference channel is automatically selected as indicated by reference number 164, and the method steps of an embodiment of automatic process 164 are illustrated in FIGS. 11A-11C.

The entire automatic method of the invention disclosed herein is under the control of the electrophysiologist (EP doctor) as indicated above. At the time of a medical procedure, there may be overriding medical or technical reasons for the EP doctor to reject a channel or the channels which have been automatically selected, so automatic method 140 includes a confirmation step 142 in which the EP doctor performing the procedure may accept or reject the channels which have been automatically selected. If the EP doctor rejects one or both of these selections, indicated by the "N" option on confirmation step 142, channel selection may be done manually or channels may be selected automatically as indicated by pathway 142*n*.

Upon final selection of ventricular and reference channels, automatic process 140 continues with the method steps of mapping as indicated by reference number 10 and as described in detail above.

FIGS. 10A and 10B are schematic diagrams of embodiment 144 of the process of automatically selecting a ventricular channel from a set of candidate MCCE channels. The ventricular channel is selected from a set of candidate channels for use within the inventive automatic method of measuring parameters of MCCE signals. It is desirable that the ventricular channel selected be a channel which exhibits high signal quality and provides a stable representation of the action of the ventricles of the heart. As mentioned above, the ventricular channel of choice is most often connected to a body surface electrode, but other channels such as an epicardial electrode or an intracardiac electrode may provide the most useful signal among the set of candidate ventricular channels.

Referring to FIG. 10A, in one embodiment of automatic process 144 for selection of the ventricular channel, an initial time period for capturing and assessing signal characteristics from all candidate channels is employed. Data is captured during the time period represented by five epochs E1 through E5. (Epochs E1 through E5 are also called sub-signals E1 through E5.) In the embodiment of FIG. 10A, this initial period is 30 seconds long. The signal from each candidate channel is an absolute-value velocity signal generated as described above. During the ventricular-channel selection process, there may be numerous possible channels being evaluated, the candidate set of channels including body-surface channels as well as some epicardial and intracardiac channels, depending on the strength of the ventricular signal in such channels. The process illustrated in FIG. 10A is applied to the waveform signals of each channel individually, generating for each channel two measures by which the ventricular-channel selection is made.

Referring again to FIG. 10A, a 30-second signal 148 from each candidate channel is divided into five 6-second epochs (sub-signals) E1 through E5. The 30-second period, 6-second epoch length and number of epochs in the initial period are not intended to be limiting. FIG. 10A illustrates the process for just one such candidate channel; a plurality of candidate channels is processed concurrently within ventricular-channel selection process 144.

As illustrated in FIG. 10A, the signals in each epoch E1-E5 are processed to determine the corresponding signal quality $SQ_i$ in method step 150. (Five such separate signal quality calculations are performed; only one is labeled with reference number 150, but the marking $SQ_i$ indicates this calculation being performed sequentially five times, each producing a value $SQ_i$ for the signal quality of the corresponding epoch $E_i$.) Signal quality calculation 150 is carried out as illustrated in FIG. 4A.

In method step 154, the five signal quality values $SQ_i$ are summed to produce an overall signal quality value $SQ_{VC}$ for each candidate ventricular channel.

Also illustrated in FIG. 10A, the signals in each epoch E1-E5 are processed in method steps 152 to determine a value for pulse interval variability $VAR_i$ for each of the five epochs (as found in the steps of FIG. 5). Five such variability calculations are performed; one is labeled with reference number 152, but the markings indicate that this calculation is performed sequentially five times, each producing a value $VAR_i$ for the variability of the corresponding epoch. In this embodiment, variability $VAR_i$ for each epoch is the difference between its maximum $MAX_{E1}$ and minimum $MIN_{E1}$ pulse-interval values during the 6-second epoch. This is illustrated for epoch E1 in the detailed method step 152*a* as follows:

$$VAR_1 = MAX_{E1} - MIN_{E1}$$

Similar relationships for each epoch are calculated to generate the variability $VAR_i$ for each epoch E1 through E5.

In method step 156, the maximum value of variability among the five values of variability is set as the variability $VAR_{VC}$ of the candidate ventricular channel.

At this stage in the automatic ventricular-channel selection process, each ventricular channel in the set of candidate ventricular channels has a channel signal quality assessment value $SQ_{VC}$ and a channel pulse-interval variability assessment value $VAR_{VC}$ which will be used to complete the automatic ventricular-channel selection process.

FIG. 10B illustrates the final portion of ventricular-channel selection process 144 for this embodiment. In general, it is desirable to select a ventricular channel with high signal quality and acceptable variability. Thus, FIG. 10B illustrates an embodiment which selects the channel with the highest signal quality but excludes channels from this choice which have especially high variability. Variability in such signals is expected. However, the reason that some channels are excluded is that these channels have variability values which are remarkably higher than those of other channels, indicating that the algorithm may be failing to detect activations properly in such channels.

In FIG. 10B, the wide arrows labeled 156*a* (two such arrows) and 154*e* represent a plurality of values as indicated. Arrows 156*a* therefore represent that the channel variability values for each of the channels are all inputs to the method steps 158 and 160. In method step 158, a ventricular-channel variability threshold $T_{VC}$ is calculated as follows:

$$T_{VC} = 2 \cdot [\text{median}(VAR_{VC}) + \Delta_{VC}]$$

where $\Delta_{VC}$ is a small increment of time which may be added into this calculation simply as a computational convenience, such as to avoid singular calculations or to avoid excluding too many channels when the variability of some channels is extremely small. The inclusion of increment $\Delta_{VC}$ in the embodiment of FIG. 10B is not intended be a limitation; $\Delta_{VC}$ may have a value of 0 or other computationally-convenient value. In FIG. 10B, $\Delta_{VC}$ has a value of 5 milliseconds.

Ventricular-channel variability threshold $T_{VC}$ is a threshold value above which the variability of a channel is deemed to be unacceptably high. In method step 160, the variability $VAR_{VC}$ for each channel is compared with ventricular-channel variability threshold $T_{VC}$, and channels for which $VAR_{VC}$ is equal to or exceeds threshold $T_{VC}$ are excluded from being the selected ventricular-channel $VC_S$.

Other computational assessments of signal quality and variability for each channel and for the exclusion of channels on the basis of high variability are of course possible. The specifics of these assessment embodiments are not intended to be limiting.

Wide arrow 154*e* represents one or more ventricular-channel signal quality values $SQ_{VC}$ for channels which have not been excluded in method step 160. Each channel represented in the set of values 154*e* is a possible selected ventricular-channel $VC_S$. In method step 162, the channel with the highest value of channel signal quality $SQ_{VC}$ is then selected as the ventricular-channel $VC_S$ within the inventive automatic method of measuring parameters of MCCE signals. (The method therefore also knows which channels are, for example, "second best" and "third best" among the candidate channels.)

After ventricular-channel $VC_S$ has been selected using ECG signals over an initial period of time (30 seconds in the embodiment of FIGS. 10A and 10B), MCCE signals from the initial period of time or from an additional period of time are used to select a reference channel to be used within the inventive automatic method of measuring parameters of MCCE signals. FIGS. 11A through 11C are schematic diagrams of embodiment 164, 166 of the process of automatically selecting a reference channel from a set of candidate channels.

Body surface electrode channels are generally known not to be good choices for reference channels for many arrhythmias; thus, the reference channel is typically selected from the remaining set of MCCE channels for use within the inventive automatic method of measuring parameters of MCCE signals. It is desirable that the reference channel selected be a channel which exhibits high signal quality and low cycle-length variability and also which exhibits a fast heart rate. For physiological reasons related to the cardiac measurements for which the present invention is intended to be used, it is also desirable that the selected reference channel indicate the shortest cycle length CL. All of these criteria are used to select a reference channel from among the set of candidate reference channels.

Referring to FIG. 11A, in automatic process 164 for selection of the reference channel, an initial time period for capturing and assessing signal characteristics from all candidate channels is employed. Data is captured during the time period represented by five epochs, labeled E6 through E10. (Epochs E6 through E10 are also called sub-signals E6 through E10.) In the embodiment of FIG. 11A, this additional initial period is 30 seconds long. The signal from each candidate reference channel is an absolute-value velocity signal generated as described above. During the reference-channel selection process, there may be numerous possible channels being evaluated. What specific channels are candidate reference channels for cardiac mapping are well-known to those skilled in electrophysiology. The process illustrated in FIG. 11A is applied to the waveform signals of each candidate channel individually, generating for each channel two measures by which the reference-channel selection is made.

Referring again to FIG. 11A, a 30-second signal 168 from each candidate channel is divided into five 6-second epochs (sub-signals) E6 through E10. The 30-second period, 6-second epoch length and number of epochs in the initial period are not intended to be limiting in any way. FIG. 11A illustrates the process for just one such candidate channel; a plurality of candidate channels is processed concurrently within reference-channel selection process 164.

As illustrated in FIG. 11A, the signals in each epoch E6-E10 are processed to determine the corresponding signal quality $SQ_i$ in method step 170. (Five such separate signal quality calculations are performed; only one is labeled with reference number 170, but the marking $SQ_i$ indicates this calculation being performed sequentially five times, each producing a value $SQ_i$ for the signal quality of the corresponding epoch $E_i$.) Signal quality calculation 170 is carried out as illustrated in the steps of FIG. 4A.

In method step 174, the five signal quality values $SQ_i$ are summed to produce an overall signal quality value $SQ_{RC}$ for each candidate reference channel.

Also illustrated in FIG. 11A, the signals in each epoch E6-E10 are processed in method steps 172 to determine a cycle length $CL_i$ and a value $VAR_i$ for cycle-length variability for each of the five epochs. The cycle length determination is performed using the method steps described in detail above and illustrated in FIGS. 6A and 6B (and as referred to in FIG. 11B). The determination of cycle-length variability (and cycle length) for each epoch is described using the schematic diagram of FIG. 11B, which illustrates this process 172a for epoch E6 as indicated by the dotted-line ellipse in FIG. 11A. Five such cycle length and cycle-length variability calculations as illustrated in FIG. 11B are performed; one is labeled with reference number 172a, but the markings of each such element in FIG. 11A indicate that this calculation is performed sequentially five times, each producing a value $VAR_i$ for the cycle-length variability of the corresponding epoch.

In the method steps illustrated in FIG. 11B, F6 is the magnitude-coincidence autocorrelation function of epoch signal E6 as calculated in method step 178. The threshold value for the magnitude-coincidence autocorrelation is a function of the noise in signal being processed as described in the summary section which defines magnitude-coincidence autocorrelation and with respect to method step 226 of FIG. 6A. Cycle length CL is computed in method step 182 as indicated, using steps outlined in FIGS. 6A and 6B. Then, in method step 186, a peak in F6 near a value of lag near 2 times CL is identified, and an interim variable DCL is set to the lag at such peak. In method step 188, another interim variable $CL_A$ is set to DCL–CL. The value for the variability $VAR_6$ of epoch E6 is then calculated as follows in method step 190:

$$VAR_6 = |CL - CL_A|$$

Similar relationships for each epoch are calculated to generate the variability $VAR_i$ for each epoch E6 through E10.

Referring again to FIG. 11A, in method step 176, three additional values (in addition to $SQ_{RC}$) are determined for each epoch E6 through E10 by which to select from among the candidate reference channels: $VAR_{RC}$; $MAX_{CL}$; and $MIN_{CL}$. $MAX_{CL}$ is the maximum cycle length $CL_i$ among the five cycle-length values. $MIN_{CL}$ is the minimum cycle length $CL_i$ among the five cycle-length values. $VAR_{RC}$ is the maximum variability value $VAR_i$ among the five variability values.

At this stage in the automatic reference-channel selection process, each reference channel in the set of candidate reference channels has a channel signal quality assessment value $SQ_{RC}$, a channel variability assessment value $VAR_{RC}$, and maximum and minimum cycle length values $MAX_{CL}$ and $MIN_{CL}$ which will be used to complete the automatic reference-channel selection process.

FIG. 11C illustrates the final portion of reference-channel selection process 164 for this embodiment. In general, it is desirable to select a reference channel with high signal quality, low variability, and short cycle length, as indicated above. FIG. 11C illustrates an embodiment which selects the channel with these characteristics.

In FIG. 11C, the wide arrows labeled 174a, 176v, 176x, and 176n each represent a plurality of values as indicated. Wide arrow 174a represents all values of $SQ_{RC}$ from the candidate reference channels; wide arrow 176v represents all values of $VAR_{RC}$ from the candidate reference channels; wide arrow 176x represents all values of $MAX_{CL}$ from the candidate reference channels; and wide arrow 176n represents all values of $MIN_{CL}$ from the candidate reference channels.

In method step 192, a figure-of-merit $FM_{RC}$ is evaluated for each candidate reference channel $FM_{RC}$ for each candidate reference channel is computed as follows:

$$FM_{RC} = SQ_{RC}/S_{RC} - MAX_{RC} - MIN_{RC} - S_{VAR} \cdot VAR_{RC}$$

where $S_{RC}$ is an arbitrary scale factor and $S_{VAR}$ is an arbitrary scale factor. The two scale factors are chosen such that a useful tradeoff within the figure-of-merit $FM_{RC}$ is created.

When signal quality values $SQ_{RC}$ are in microvolts and cycle lengths are in milliseconds, a value of $S_{RC}$ of 32 and a value of $S_{VAR}$ of 2 have been found to yield a useful tradeoff among cycle lengths, variability, and signal quality and also to be computationally convenient.

The $FM_{RC}$ values for each candidate reference channel are output from method step 192 as indicated by wide arrow 194. In method step 196, the channel with the highest value of $FM_{RC}$ is the selected reference-channel $RC_S$.

Other computational assessments of signal quality, variability, and cycle length for each channel are of course possible. The specifics of these assessment embodiments are not intended to be limiting.

As described above, one aspect of the inventive automatic method of measuring parameters of multi-channel cardiac electrogram signals includes the ability to compensate for signal degradation in the reference channel during the creation of an activation map by selecting a new reference channel and recreating the set of LAT measurements based on the new reference channel and generating a new map. During the initial selection process for the reference channel, the inventive method keeps track of the reference channels which have values for $FM_{RC}$ just below the selected reference channel $RC_S$ so that if necessary, these "second best" reference channels can be substituted for the selected reference channel and the mapping process can continue without losing the valuable time and effort that has already been spent on the mapping process.

In another aspect of the inventive method, multiple mapping channels may also be employed, and the processing steps outlined herein applied to multiple mapping channels as well as multiple reference channels. Some catheters which are used in cardiac procedures may include multiple electrodes in a variety of configurations. In addition, multiple catheters may be employed. The speed of computer processing available enables numerous calculations to be done very rapidly such that multiple mapping channels may be supported to generate a plurality of maps as the EP doctor moves the mapping electrodes throughout chambers and vessels of the heart.

FIG. 12 is a matrix which schematically illustrates a series of reference channels and mapping channels from among a set of MCCE signals which in an aspect of the inventive method may be processed in parallel to generate multiple LAT maps as well as track the other cardiac parameters measured with the inventive method in a variety of combinations of reference and mapping channels. Some channels may be displayed for the EP doctor in parallel while others may serve of possible backups in case of signal degradation as explained above.

Referring to FIG. 12, the table 260 shown is an 8×8 matrix (eight reference channels $R_1$ through $R_8$ and eight mapping channels $M_1$ through $M_8$. The number of channels illustrated is not intended to be limiting, but rather to illustrate the concept of flexible configuration combinations of reference and mapping channels. In fact, a set of MMCE signals is typically much larger than the eight illustrated here. Eight channels in the MCCE set of signals is only for purposes of illustration.) The "√" symbols indicate that the mapping channel and reference channel at such an intersection together can generate a map. In other words, as shown in table 260 of FIG. 12, each channel $M_1$ through $M_8$ can be paired with any other channel $R_1$ through $R_8$, and any combination of these pairings can be created. The "-" simply indicate redundancy in table 260. The "-" symbol is located along the diagonal of table 260 indicating that any channel is not usefully paired with itself. Further, some channels among the set of channels may in fact be ventricular channels (primarily exhibiting ventricular signal characteristics) and therefore also not good candidates for either a reference or mapping channel.

The advantages of such multiple-channel processing configurations are that procedure time may be shortened but also that a much richer array of measurements may be obtained to provide better information to the EP doctor to ameliorate the cardiac deficiency being treated. Further, as described above, backup channels can be available to deal with lost or degraded signals during a procedure without the need to start the procedure over again.

It is possible in some multi-channel configurations that certain information may be shared among several parallel computations. For example, it is possible that ventricular pulse interval values may be used for the determination of several reference-channel cycle lengths, and ventricular-channel activation times may be shared for use with more than one mapping channel. And many other combinations other than those exampled here are possible with the multi-channel processing of the inventive method described herein.

In embodiment 10 of the inventive automatic method of measuring parameters of multichannel cardiac signals described in detail above, contiguous 6-second epochs of MCCE signal data are used. Alternatively, a moving-window format of selecting epoch starting and end points may be used, such as the next epoch in a series of epochs consisting of the last 5 seconds of the previous epoch and a new sixth second. Other epoch-forming strategies may be used, depending on the computational advantages which may be possible and on the desired speed of analysis.

Figure 13:
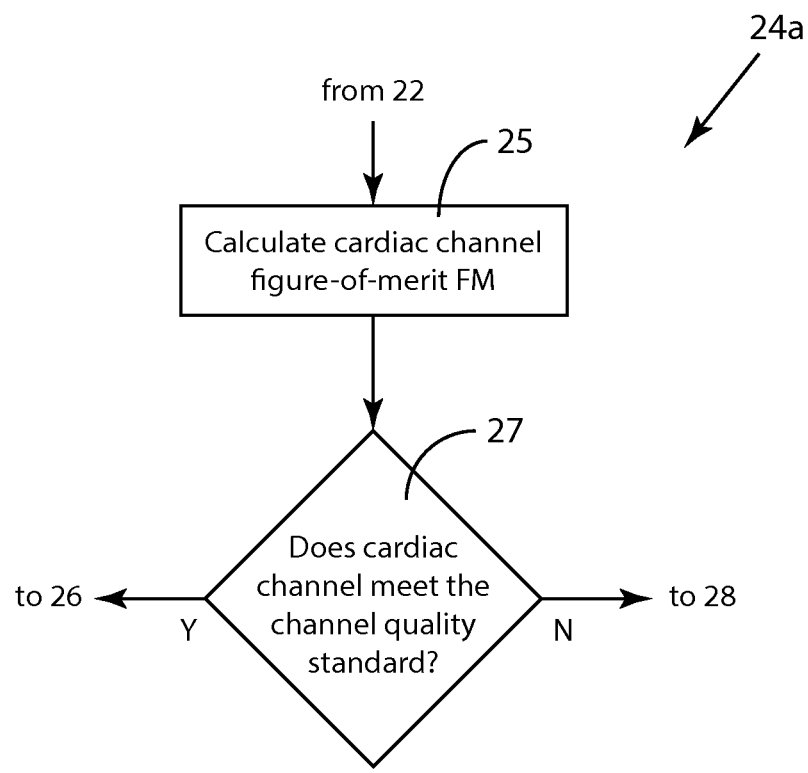
FIG. 13 is a schematic block diagram illustrating an alternative embodiment of the monitoring of cardiac channel quality. The alternative embodiment replaces a portion of the schematic block diagram of FIG. 1.

FIG. 13 is a schematic block diagram illustrating an alternative embodiment of the monitoring of cardiac channel quality. The alternative embodiment replaces a portion of the schematic block diagram of FIG. 1. As previously described and as illustrated in FIG. 1 and in FIG. 4A, signal quality is defined as a quantity dependent on signal strength, signal irregularity and noise. In addition to such a specific assessment of signal quality, an overall channel quality assessment may include information on the variability of the cycle length (or pulse interval when considering ventricular channels). Such an overall assessment for a reference is represented by a figure-of-merit which reflects the fact that higher signal quality values and lower cycle-length variability are desirable.

In order to make an assessment of overall channel quality during ongoing operation of the inventive method, one embodiment of such a system includes applying the steps of automatic channel selection for initialization in real-time to monitor channel quality. These channel selection steps are fully described above and illustrated in FIGS. 9-11C. As described in these embodiments, assessment of overall channel quality includes calculation of various signal quantities over a plurality of epochs. In these embodiments, five contiguous 6-second epochs are evaluated as shown in FIGS. 10A-11C. The number of epochs may vary and the length of the epochs may also differ from 6 seconds. Further, signal parameters may be computed over moving time windows rather than sequential (contiguous) epochs. The epochs may be of fixed-length or of various lengths. Any number of variations of time periods are possible in the computation of the elements of channel figures-of-merit, signal quality and cycle-length or pulse-interval variability.

The schematic of FIG. 13, labeled with reference number 24a, replaces element 24 in FIG. 1 in the alternative embodiment of FIG. 13. The connections to the block diagram are shown as connections with elements 22, 26 and 28 of FIG. 1. The functional elements 25 and 27 represent the alternative functions of calculating a figure-of-merit FM (element 25) and using figure-of-merit FM in comparison to a channel quality standard (element 27). Such a standard may be preset threshold value that figure-of-merit FM must exceed or it may be a dynamically-determined standard such as being the highest figure-of-merit FM among a set of candidate channels. Other standards are also possible such as, for example, a combination of a preset threshold value and the maximum among a set of channels. In such a case, a channel has acceptable overall quality when it has a figure-of-merit FM which is both the highest in a set of channels and is above a preset threshold value.

The calculation of figure-of-merit FM as illustrated in FIG. 13 involves the application of the steps of FIGS. 10A and 10B for the assessment of overall quality for candidate ventricular channels and application of the steps of FIGS. 11A-11C for the assessment of the overall quality for candidate reference channels. As described above, various strategies for determining the timing of signals used are possible.

In this inventive method, a plurality of channels are stored and processed such that the monitoring of overall channel quality is possible for cardiac channels as desired. The inventive method includes a variety of strategies for monitoring overall cardiac channel quality, including (a) performing the necessary calculations in real-time for only one or more of the "active" channels (the currently used mapping, ventricular, and reference channels for LAT determination), (b) performing the necessary calculations in real-time for the entire plurality of cardiac channels, and (c) performing such calculations for a subset of cardiac channels. Since channel signal data is stored, if a strategy such as (a) is chosen, overall channel quality of other ("non-active") channels can be performed when necessary to determine which channel will replace the current cardiac channel. If a strategy such as (c) is employed, the inventive method monitors every cardiac channel, making an up-to-date assessment of the overall channel quality for every cardiac channel in the system available at any time.

Figure 14:
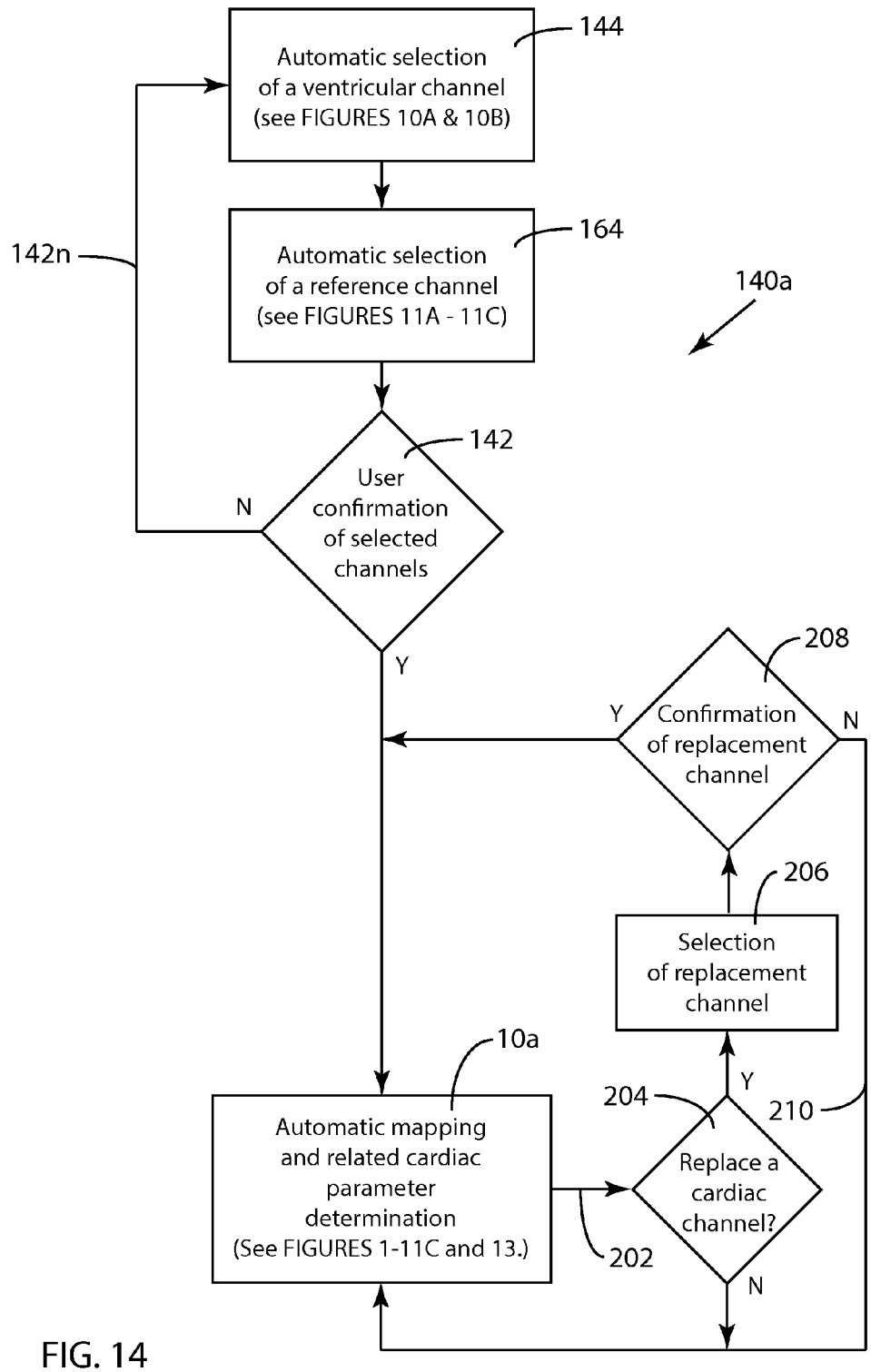
FIG. 14 is a schematic block diagram illustrating an alternative embodiment of the channel selection method illustrated in FIG. 9, adding elements of the automatic channel selection steps within initialization to the real-time operation of the inventive method for measuring parameters of MCCE signals such that cardiac channels may be replaced when the quality of a channel signal degrades during operation of the inventive method.

FIG. 14 is a schematic block diagram illustrating an alternative embodiment of the channel selection method illustrated in FIG. 9, adding to real-time operation the steps of automatic channel selection which in the embodiment of FIG. 9 operate only within the initialization process. The method steps of FIG. 14, indicated together as 140a, include not only the initialization steps from the embodiment of FIG. 9 but also elements 202 through 210. Element 10a, as shown, is a modification of element 10 in FIG. 9, modified to include the now real-time automatic steps embodied in FIGS. 10A-11C and 13. Elements 202 through 210 describe an embodiment which carries out cardiac channel replacement during real-time operation of the inventive method, replacing a reference or ventricular channel when the overall quality of such channel degrades during operation.

Method element 10a encompasses the running (real-time) operation of the inventive method as detailed in FIGS. 1-11C and 13. Connection 202 and method element 204 illustrate the step of deciding if a cardiac channel needs to be replaced, the result of calculating figure-of-merit FM in step 25 and making a comparison with a channel quality standard in step 27 (see FIG. 13). A user alert is generated in step 28 (see FIG. 1), and decision step 204 may proceed in a completely automatic fashion if the user chooses such automatic functioning. In such a case, an alert at step 28 is still provided to the user. However, it is anticipated that the user may intervene in the automatic steps of channel replacement to exercise more control over the replacement process. An "N" decision in decision step 204 returns the process to overall running-time operation represented in element 10a.

The inventive method in embodiment 140a proceeds to method element 206 in which a replacement channel is selected, either automatically or manually by the user, based on assessments of possible replacement cardiac channels. Embodiment 140a proceeds then to method step 208 in which confirmation of the channel replacement is carried out, either automatically or by user intervention. With a "Y" decision at decision step 208, the process continues channel replacement and updating in element 210 and then the process continues with overall running-time operation represented in element 10a. An "N" decision at decision step 208 returns the process to overall running-time operation represented in element 10a without channel replacement and updating.

In the embodiments of FIGS. 10A through 11C, the assessments of overall channel signal quality differ for candidate reference channels and candidate ventricular channels. Skilled practitioners in the use of cardiac channel signals and in electrophysiology are able to determine which cardiac channels may serve as possible reference channels as well as those cardiac channels which have the properties of ventricular channels. Herein, the set of candidate reference channels is also referred to as a first subset of cardiac channels, and the set of candidate ventricular channels is also referred to as a second subset of cardiac channels.

While the principles of this invention have been described in connection with specific embodiments, it should be understood clearly that these descriptions are made only by way of example and are not intended to limit the scope of the invention.

The invention claimed is:

1. An automatic method of determining local activation time (LAT) in multi-channel cardiac electrogram signals including a plurality of cardiac channels, the method comprising:
    storing the cardiac channel signals;
    selecting a mapping channel, a ventricular channel, and a reference channel from among the plurality of cardiac channels;
    using the selected channels to compute first LAT values at a plurality of mapping-channel locations;
    monitoring the quality of at least one selected channel;
    if the quality of a monitored cardiac channel falls below a standard, replacing the sub-standard channel with another channel of the plurality of channels having an above-standard quality; and
    computing second LAT values based on the replacement cardiac channel.

2. The automatic LAT-determination method of claim 1 wherein computing second LAT values based on the replacement cardiac channel includes computing second LAT values for previous mapping-channel locations.

3. The automatic LAT-determination method of claim 1 further including displaying the first LAT values as a first LAT map, and if second LAT values are computed, generating a second LAT map based on the second LAT values.

4. The automatic LAT-determination method of claim 1 wherein the replaced and replacement channels are reference channels.

5. The automatic LAT-determination method of claim 4 wherein monitoring the signal quality of a cardiac channel includes:
    generating a velocity-dependent signal from the monitored channel signal over a preset time window;
    finding the median value MED of the velocity-dependent signal over the preset time window;

dividing the velocity-dependent signal into a plurality of signal chunks;
finding the chunk-maximum within each chunk;
finding the maximum MAX and minimum MIN values among the plurality of chunk-maxima; and
computing a channel signal quality SQ based on MAX, MIN and MED.

6. The automatic LAT-determination method of claim 5 wherein the channel signal quality SQ is computed as $2 \times MIN - MAX - K_1 \times MED$ where $K_1$ is a constant.

7. The automatic LAT-determination method of claim 6 wherein each signal chunk is of equal length.

8. The automatic LAT-determination method of claim 7 wherein each velocity-dependent signal is divided into three equal-length chunks.

9. The automatic LAT-determination method of claim 8 wherein computing second LAT values based on the replacement cardiac channel includes computing second LAT values for previous mapping-channel locations.

10. The automatic LAT-determination method of claim 8 further including displaying the first LAT values as a first LAT map, and if second LAT values are computed, generating a second LAT map based on the second LAT values.

11. The automatic LAT-determination method of claim 5 wherein the preset time window is about 6 seconds long.

12. The automatic LAT-determination method of claim 11 wherein the channel signal quality is computed as $2 \times MIN - MAX - K_1 \times MED$ where $K_1$ is a constant.

13. The automatic LAT-determination method of claim 12 wherein $K_1$ is about 4.

14. The automatic LAT-determination method of claim 13 wherein each signal chunk is of equal length.

15. The automatic LAT-determination method of claim 14 wherein each velocity-dependent signal is divided into three equal-length chunks.

16. The automatic LAT-determination method of claim 15 wherein computing second LAT values based on the replacement cardiac channel includes computing second LAT values for previous mapping-channel locations.

17. The automatic LAT-determination method of claim 15 further including displaying the first LAT values as a first LAT map, and if second LAT values are computed, generating a second LAT map based on the second LAT values.

18. The automatic LAT-determination method of claim 1 wherein monitoring the quality of cardiac channels includes monitoring cycle-length variability of each channel of a first subset of the monitored channels.

19. The automatic LAT-determination method of claim 18 wherein the first-subset cycle-length variability monitoring includes determining a maximum cycle length $MAX_{CL}$, a minimum cycle length $MIN_{CL}$, and a cycle-length variability $VAR_{RC}$ for each monitored first-subset channel.

20. The automatic LAT-determination method of claim 19 wherein determining a maximum cycle length $MAX_{CL}$, a minimum cycle length $MIN_{CL}$, and a cycle-length variability $VAR_{RC}$ includes for each monitored first-subset channel:
selecting a set of sequential sub-signals;
estimating cycle lengths and cycle-length variability for each sub-signal;
selecting $MAX_{CL}$ and $MIN_{CL}$ as the maximum and minimum of the sub-signal cycle lengths; and selecting $VAR_{RC}$ as the maximum sub-signal variability.

21. The automatic LAT-determination method of claim 20 wherein estimating the cycle length of each sub-signal includes:
estimating pulse intervals in the ventricular channel;
generating a velocity-dependent signal from the sub-signal over a preset time window;
autocorrelating the sub-signal velocity-dependent signal;
selecting a peak value of the autocorrelation based on ventricular pulse-interval estimates; and
setting the sub-signal cycle length CL to the lag value of the selected peak in the autocorrelation.

22. The automatic LAT-determination method of claim 21 wherein estimating sub-signal cycle-length variability includes:
estimating the lag DCL at an autocorrelation peak near twice CL;
computing an intermediate cycle-length $CL_A$; and
computing sub-signal cycle-length variability as the absolute value of the difference between CL and $CL_A$.

23. The automatic LAT-determination method of claim 20 wherein the sub-signals are of equal length.

24. The automatic LAT-determination method of claim 23 wherein the sub-signals are about 6 seconds long.

25. The automatic LAT-determination method of claim 24 wherein the set of sub-signals comprises 5 sub-signals.

26. The automatic LAT-determination method of claim 25 wherein estimating the cycle length of each sub-signal includes:
estimating pulse intervals in the ventricular channel;
generating a velocity-dependent signal from the sub-signal over a preset time window;
autocorrelating the sub-signal velocity-dependent signal;
selecting a peak value of the autocorrelation based on ventricular pulse-interval estimates; and
setting the sub-signal cycle length CL to the lag value of the selected peak in the autocorrelation.

27. The automatic LAT-determination method of claim 26 wherein estimating sub-signal cycle-length variability includes:
estimating the lag DCL at an autocorrelation peak near twice CL;
computing an intermediate cycle-length $CL_A$; and
computing sub-signal cycle-length variability as the absolute value of the difference between CL and $CL_A$.

28. The automatic LAT-determination method of claim 20 wherein monitoring the quality of cardiac channels further includes for each first-subset channel:
determining a signal quality value $SQ_i$ for each sub-signal;
summing the sub-signal signal quality values $SQ_i$ to generate a first-subset channel signal quality value $SQ_{RC}$; and
computing a first-subset channel figure-of-merit $FM_{RC}$.

29. The automatic LAT-determination method of claim 28 wherein the figure-of-merit $FM_{RC}$ is computed as $SQ_{RC}/K_2 - MAX_{CL} - MIN_{CL} - K_3 \times VAR_{RC}$ where $K_2$ and $K_3$ are constants.

30. The automatic LAT-determination method of claim 29 wherein the of $K_2$ is about 32 and the value of $K_3$ is about 2.

31. The automatic LAT-determination method of claim 29 wherein if the quality of a monitored first-subset channel falls below a standard, replacing the sub-standard first-subset channel with another first-subset channel having a higher figure-of-merit.

32. The automatic LAT-determination method of claim 31 wherein the of $K_2$ is about 32 and the value of $K_3$ is about 2.

33. The automatic LAT-determination method of claim 1 wherein monitoring the quality of cardiac channels includes monitoring pulse-interval variability of each channel of a second subset of the monitored channels.

34. The automatic LAT-determination method of claim 33 wherein the second-subset pulse-interval variability monitoring includes for each monitored second-subset channel:
- selecting a set of sequential sub-signals;
- for each sub-signal, determining a maximum pulse interval $MAX_{Ei}$ and a minimum pulse-interval $MIN_{Ei}$;
- for each sub-signal, computing a sub-signal pulse-interval variability $VAR_i$ as $MAX_{Ei}-MIN_{Ei}$; and
- computing a second-subset channel pulse-interval variability $VAR_{VC}$ as the maximum value among the sub-signal pulse-interval variability values $VAR_i$.

35. The automatic LAT-determination method of claim 34 wherein the sub-signals are of equal length.

36. The automatic LAT-determination method of claim 35 wherein the sub-signals are about 6 seconds long.

37. The automatic LAT-determination method of claim 34 wherein the set of sub-signals comprises 5 sub-signals.

38. The automatic LAT-determination method of claim 34 wherein monitoring the quality of cardiac channels further includes for each second-subset channel:
- determining a signal quality value $SQ_i$ for each sub-signal; and
- summing the sub-signal signal quality values $SQ_i$ to generate a second-subset channel signal quality value $SQ_{VC}$.

39. The automatic LAT-determination method of claim 34 wherein if the quality of a monitored second-subset channel falls below a standard, replacing the sub-standard second-subset channel with another second-subset channel having a higher channel signal quality $SQ_{VC}$.

40. The automatic LAT-determination method of claim 39 wherein the channel pulse-interval variability $VAR_{VC}$ of the another second-subset channel is below a computed threshold pulse-interval variability $T_{VC}$.

41. The automatic LAT-determination method of claim 40 wherein threshold $T_{VC}$ is proportional to the median of all second-subset channel pulse-interval variability values $VAR_{VC}$.

42. The automatic LAT-determination method of claim 18 wherein monitoring the quality of cardiac channels further includes monitoring pulse-interval variability of each channel of a second subset of the monitored channels.

43. The automatic LAT-determination method of claim 1 wherein monitoring the quality of a cardiac channel includes estimating an LAT measurement confidence interval and comparing the estimate with a measurement-confidence criterion.

44. The automatic LAT-determination method of claim 43 wherein estimating an LAT measurement confidence interval includes:
- estimating the cycle-length CL of the reference channel;
- selecting an activation at a time $t_M$ in the mapping-channel signal;
- identifying a plurality of activations at times $t_R$ in the reference channel;
- computing a plurality of LAT values with respect to the values of $t_R$;
- selecting a subset of the plurality of LAT values; and
- estimating the LAT measurement confidence interval as the difference between the maximum and minimum LAT values in the subset.

45. The automatic measuring method of claim 44 wherein the subset comprises the interquartile values of the plurality of LAT values.

46. The automatic LAT-determination method of claim 1 wherein monitoring the quality of a cardiac channel includes estimating a channel cycle-length confidence interval.

47. The automatic LAT-determination method of claim 46 wherein estimating a channel cycle-length confidence interval includes estimating channel cycle-length by:
- estimating pulse intervals in the ventricular channel;
- generating a velocity-dependent signal from the channel signal over a preset time window;
- autocorrelating the channel velocity-dependent signal;
- selecting a peak value of the autocorrelation based on ventricular pulse-interval estimates; and
- setting the channel cycle length CL to the lag value of the selected peak in the autocorrelation.

48. The automatic LAT-determination method of claim 47 wherein estimating a channel cycle-length confidence interval includes:
- determining the lag value L2 at a peak in the autocorrelation near twice CL; and
- estimating the channel cycle-length confidence interval as a function of the difference between L2 and twice CL.

49. The automatic LAT-determination method of claim 1 wherein monitoring the quality of a cardiac channel includes estimating a channel pulse-interval confidence interval.

50. The automatic LAT-determination method of claim 49 wherein estimating a channel pulse-interval confidence interval includes estimating channel pulse-interval by:
- generating a velocity-dependent signal from the channel signal over a preset time window;
- identifying a plurality of activation times in the channel velocity-dependent signal;
- computing a set of activation intervals;
- identifying maximum and minimum activation intervals in the set; and
- setting the confidence interval equal to the difference between the maximum and minimum activation intervals.

* * * * *